(12) United States Patent
Lee et al.

(10) Patent No.: US 7,355,081 B2
(45) Date of Patent: *Apr. 8, 2008

(54) CURCUMIN ANALOGUES AND USES THEREOF

(75) Inventors: Kuo-Hsiung Lee, Chapel Hill, NC (US); Li Lin, Chapel Hill, NC (US); Charles C-Y Shih, Solana Beach, CA (US); Ching-Yuan Su, San Diego, CA (US); Junko Ishida, Tokyo (JP); Hironori Ohtsu, Matsubara (JP); Hui-Kang Wang, San Diego, CA (US); Hideji Itokawa, Chapel Hill, NC (US); Chawnshang Chang, Pittsford, NY (US)

(73) Assignees: The University of North Carolina at Chapel Hill, Chapel Hill, NC (US); The University of Rochester Medical Center, Rochester, NY (US); Androscience Corporation, San Diego, CA (US)

( * ) Notice: Subject to any disclaimer, the term of this patent is extended or adjusted under 35 U.S.C. 154(b) by 404 days.

This patent is subject to a terminal disclaimer.

(21) Appl. No.: 10/966,723

(22) Filed: Oct. 15, 2004

(65) Prior Publication Data
US 2005/0187255 A1 Aug. 25, 2005

Related U.S. Application Data

(63) Continuation-in-part of application No. PCT/US03/09350, filed on Mar. 27, 2003.

(51) Int. Cl.
*C07C 49/15* (2006.01)
(52) U.S. Cl. .......................... 568/36; 568/325; 580/53; 514/544
(58) Field of Classification Search .................. None
See application file for complete search history.

(56) References Cited

FOREIGN PATENT DOCUMENTS

| WO | WO 95/18606 | 6/1995 |
|---|---|---|
| WO | WO 97/16403 | 5/1997 |
| WO | WO 99/22728 | 5/1999 |
| WO | WO 01/30335 | 5/2001 |
| WO | WO 01/40188 | 6/2001 |

OTHER PUBLICATIONS

Ohtsu et al. "Anti-Tumor Agents 222. Synthesis and Anti-androgen Activity of New Diarylheptanoids" Biorganic & Medicinal Chemistry 11: 5083-5090 (2003).*
Anto et al; "Anti-tumour and free radical scavenging activity of synthetic curcuminoids" *International Journal of Pharmaceutics.* 131 1-7 (1996).
Berzin et al; "Identification of natural curcumins" *Bioorganicheskaya Khirniya.* 22: 10-11 823-831 (1996).
Chowdhury et al; "Isolation, characterization and insect growth inhibitory activity of major turmeric constituents and their derivatives against Schistocerca gregaria (Forsk) and Dysdercus koenigii (Walk)" *Pest Management Science.* 56 1086-1092 (2000).
Hahm et al; "New and known symmetrical curcumin derivatives inhibit the formation of Fos-Jun DNA complex" *Cancer Letters.* 184 89-96 (2000).
Masuda et al; "Antioxidative Curcuminoids from Rhizomes of Curcuma Xanthorrhiza" *Phytochemistry.* 31:10 3645-3647 (1992).
Ohtsu et al; "Antitumor Agents 217 Curcumin Analogues as Novel Androgen Receptor Antagonists with Potential as Anti-Prostate Cancer Agents" *Journal of Medicinal Chemistry.* 45 5037-5042 (2002).
European Search Report for 03718072.6-1521/US0309350. Date of mailing May 10, 2005.
Arbiser, Jack L., et al., Curcumin is an In Vivo Inhibitor of Angiogenesis, *Molecular Medicine*, vol. 4, pp. 376-383 (1998).
Choshi et al., Synthesis of Dibenzoylmethane Derivatives and Inhibition of Mutagenicity in Salmonella Typhimurium, *Chem. Abstract.*, vol. 117, No. 48036 (1992).
Gorbitz, C.H. et al., Structural Studies of Curcuminoids, V. Crystal Structures of 1,7,-bis (3, 4-dimethoxyphenyl)-4-benzyl-1, 6-heptadiene-3, 5-dione and 1,7-bis (4-hydroxy-3 methoxyphenyl)-4-(2-oxo-2-ethoxyethyl)-1, 6-heptadiene-3, 5-dione, *Chem. Abstract.*, vol. 107, No. 6988 (1986).
Ishida, Junko, et al., Antitumor-promoting effects of cyclic diarylheptanoids on Epstein-Barr virus activation and two-stage mouse skin carcinogenesis, *Cancer Letters*, vol. 159, pp. 135-140 (2000).
Martono, S., Inhibitory Effects of Curcumin and its Analogs on In Vitro Rat Liver Glutathione S-Transferases Activity, *Chem. Abstract.*, vol. 128, No. 110377 (1996).
McDonald et al., Synthesis and Anticancer Activity of nordihydrogualaretic Acid and Analogues, *Chem. Abstract.*, vol. 138, No. 362138 (2001).
Nurfina, A. N., et al., Synthesis of some symmetrical curcumin derivatives and their anti-inflammatory activity, *Eur. J. Med. Chem.*, vol. 32, pp. 321-328, (1997).
Parveen, I., et al., Labeled Compounds of Interest as Antitumor Agents, *Chem. Abstract.*, vol. 133, No. 281645 (2000).
Pedersen et al., Synthesis of Naturally Occurring Curcuminoids and Related Compounds, *Chem. Abstract.*, vol. 103, No. 178092 (1985).
Ruby, A.J., et al., Anti-tumour and antioxidant activity of natural curcuminoids, *Cancer Letters*, vol. 94, pp. 79-83 (1995).

(Continued)

*Primary Examiner*—Yvonne Eyler
*Assistant Examiner*—Yate' K Cutliff
(74) *Attorney, Agent, or Firm*—Myers Bigel Sibley & Sajovec, P.A.

(57) ABSTRACT

The present invention relates to compounds capable of acting as androgen receptor antagonists, pharmaceutical formulations containing the same, and methods of use thereof. Such uses include, but are not limited to, use as antitumor agents, particularly for the treatment of cancers such as colon, skin and prostate cancer and to induce androgen receptor antagonist activity in a subject afflicted with an androgen-related affliction. Examples of androgen-related afflictions include, but are not limited to, baldness, hirsutism, behavioral disorders, acne, and uninhibited spermatogenesis wherein inhibition of spermatogenesis is so desired.

9 Claims, 5 Drawing Sheets

OTHER PUBLICATIONS

Suglyama, Yasunori, et al., Involvement of the β-Diketone Moiety in the Antioxidantive Mechanism of Tetrahydrocurcumin, *Biochemical Pharmacology*, vol. 52, pp. 519-525 (1996).

Syu, Wan-Jr., et al., Cytotoxicity of Curcuminoids and Som Novel Compounds from Curcuma zedoaria, *J. Nat. Prod.*, vol. 61, pp. 1531-1534 (1998).

International Search Report corresponding to PCT/US03/09350 dated Dec. 19, 2003.

International Search Report for Application No. PCT/US2005/36522 mailed on Apr. 24, 2006.

Devasena et al. "Bis-1,7-(2-Hydroxyphenyl)-Hepta-1,6-Diene-3,5-Dione (A Curcumin Analog) Ameliorates DMH-Induced Hepatic Oxidative Stress During Colon Carcinogenesis" *Pharmacological research* 43(1): 39-45 (2002).

Sakano et al. "Metal-Mediated DNA Damage Induced by Curcumin in the Presence of Human Cytochrome P450 Isozymes" *Archives of Biochemistry and Biophysics* 405: 223-230 (2002).

Ishida et al. "Antitumore Agents. Part 214: Synthesis and Evaluation of Curcumin Analogues as Cytotoxic Agents" *Bioorganic & Medicinal Chemistry* 10: 3481-3487 (2002).

Ireson et al. "Characterization of Metabolites of the Chemopreventive Agent Curcumin in Human and Rat Hepatocytes and in the Rat in Vivo, an Evaluation of Their Ability to Inhibit Phorbol Ester-Induced Prostaglandin $E_2$ Production" *Cancer Research* 61: 1058-1064 (2001).

Ahsan et al. "Pro-oxidant, Anti-oxidant and Cleavage Activities on DNA of Curcumin and its Derivatives Demethoxycurcumin and bisdemethoxycurcumin" *Chemico-Biological Interactions* 121: 161-175 (1999).

Anto et al. "Anti-Tumore and Free Radical Scavenging Activity of Synthetic Curcuminoids" *International journal of Pharmaceutics* 131: 1-7 (1996).

Ohtsu et al. "Antitumore Agents 222. Synthesis and Anti-androgen Activity of New Diarylheptanoids" *Bioorganic & Medicinal Chemistry* 11: 5083-5090 (2003).

* cited by examiner

| | R₁ | R₂ | R₃ | R₄ |
|---|---|---|---|---|
| 1 | OCH₃ | OCH₃ | H | H |
| 2 | OCH₃ | H | H | H |
| 3 | H | H | H | H |
| 4 | OCH₃ | OCH₃ | CH₃ | CH₃ |

| | R₁ | R₂ | R₃ | R₄ |
|---|---|---|---|---|
| 5 | OCH₃ | OCH₃ | H | H |
| 6 | OCH₃ | H | H | H |
| 7 | H | H | H | H |
| 8 | OCH₃ | OCH₃ | CH₃ | CH₃ |

| | R₁ | R₂ |
|---|---|---|
| 9 | H | H |
| 10 | CH₃ | CH₃ |

| | R₆ | R₇ |
|---|---|---|
| 11 | =O | =O |
| 12 | =O | -OH |
| 13 | -OH | -OH |

| | R₅ | R₆ | R₇ |
|---|---|---|---|
| 14 | H | =O | =O |
| 15 | H | =O | -OH |
| 16 | H | -OH | -OH |
| 17 | CH₃ | =O | -OH |
| 18 | CH₃ | -OH | -OH |

| | R₁ | R₃ | R₄ |
|---|---|---|---|
| 19 | OCH₃ | CH₂COOCH₃ | H |
| 20 | OCH₃ | CH₂COOCH₃ | CH₂COOCH₃ |

|    | R₁   | R₃ | R₈      |
|----|------|----|---------|
| 21 | H    | H  | COOH    |
| 22 | OCH₃ | OH | COOC₂H₅ |
| 23 | OCH₃ | OH | COOH    |

|    | R₁ | R₂  | R₃   | R₄ |
|----|----|-----|------|----|
| 24 | H  | H   | F    | H  |
| 25 | H  | F   | H    | H  |
| 26 | F  | H   | H    | H  |
| 27 | H  | F   | OMe  | H  |
| 28 | H  | CF₃ | F    | H  |
| 29 | H  | H   | OCF₃ | H  |

|    | R₁  | R₂ | R₃     |
|----|-----|----|--------|
| 30 | H   | H  | C=O    |
| 31 | H   | H  | C=N-OH |
| 32 | CH₃ | OH | C=O    |

|    | R₁  | R₂  | R₃     |
|----|-----|-----|--------|
| 33 | H   | H   | C=O    |
| 34 | CH₃ | H   | C=O    |
| 35 | CH₃ | CH₃ | C=O    |
| 36 | Ac  | Ac  | C=O    |
| 37 | H   | H   | O-O    |
| 38 | H   | H   | S-S    |

|    | R₁   | R₂   | R₃   | R₃'  | R₄     |
|----|------|------|------|------|--------|
| 39 | H    | OCH₃ | OCH₃ | OCH₃ | H      |
| 40 | OCH₃ | H    | OCH₃ | OCH₃ | H      |
| 41 | H    | H    | OCH₃ | NO₂  | Br     |
| 42 | H    | H    | NO₂  | NO₂  | Br     |
| 43 | H    | H    | NO₂  | NO₂  | H      |
| 44 | H    | H    | H    | H    | CH₂CO  |

CURCUMIN ANALOGUES AND USES THEREOF

RELATED APPLICATIONS

This application is a continuation-in-part of PCT International Application No. PCT/US2003/009350, filed Mar. 27, 2003, titled Novel Curcumin Analogues and Uses Thereof, published in English on Oct. 30, 2003, which claims priority from U.S. patent application Ser. No. 10/124,642, filed Apr. 17, 2002, titled Novel Curcumin Analogues and Uses Thereof, now issued as U.S. Pat. No. 6,790,979, the disclosures of which are incorporated by reference herein in their entirety.

STATEMENT OF FEDERAL SUPPORT

This invention was made with Government support under Grant No. CA-17625 and Grant No. CA-55639. The government has certain rights in this invention.

FIELD OF THE INVENTION

The present invention relates to compounds capable of acting as androgen receptor antagonists, pharmaceutical formulations containing the same, and methods of use thereof.

BACKGROUND OF THE INVENTION

The androgen receptor (AR) is a member of a large family of ligand-dependent transcriptional factors known as the steroid receptor superfamily. Chang et al., *Proc. Natl. Acad. Sci. USA*, 85, 7211-7215 (1988). Beato, M., *Cell*, 56, 335-344 (1989). Androgens and the AR play an important role in the growth of the normal prostate and prostate cancer. Prostate cancer represents the most common male malignancy in the United States. Landis et al., *Cancer J. Clin.*, 48, 6-29 (1998). Recently, antiandrogens such as hydroxyflutamide (HF) in combination with surgical or medical castration have been widely used for the treatment of prostate cancer. Crawford et al., *New Engl. J. Med.*, 321, 419-424 (1989). Several compounds, including cyprosterone, HF, and bicalutamide (shown below), have been used clinically in the treatment of prostate cancer.

Chart 1.
Structures of cyprosterone, hydroxyflutamide, and bicalutamide

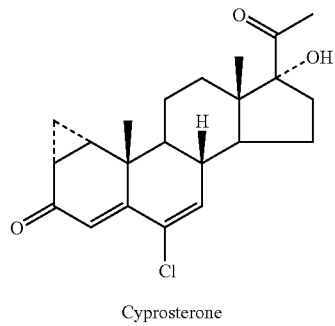

Cyprosterone

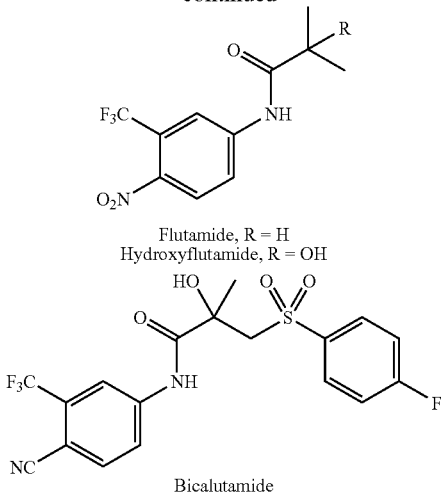

Flutamide, R = H
Hydroxyflutamide, R = OH

Bicalutamide

The synthetic steroidal antiandrogen cyprosterone is one of the first antiandrogens used clinically in Europe, McLeod, D., G., *Cancer*, 71, 1046-1049 (1993) but it has many side effects. Neumann et al., *J. Clin. Oncol.*, 1, 41-65 (1982). HF and bicalutamide are both nonsteroidal antiandrogens. Bicalutamide is a newer nonsteroidal antiandrogen originally thought to have a pure antiandrogen activity without agonist activity. It has a longer half-life (6 days) and a higher binding affinity to the AR than HF. Verhelst et al., *Clin. Endocrinol.*, 41, 525-530 (1994). (a) Kelly et al., *J. Urol.* (1993), 149, 607-609; (b) Scher et al., Prostate Cancer. *J. Clin. Oncol.*, 11, 1566-1572 (1993).

Although antiandrogen hormone therapy has been widely used for the treatment for prostate cancer, some antiandrogens may act as AR agonists which may result in "antiandrogen withdrawal syndrome." Miyamoto et al., *Proc. Natl. Acad. Sci. USA*, 95, 7379-7384 (1998). A currently accepted hypothesis postulates that mutations in androgen receptors may account for why HF, the active metabolite of flutamide, can activate androgen receptor target genes and stimulate prostate cancer growth. Miyamoto et al., *Proc. Natl. Acad. Sci. USA*, 95, 7379-7384 (1998). The same mechanism is used to explain the "flutamide withdrawal syndrome," in which patients who experience an increase in prostate-specific antigen (PSA) while taking flutamide, have a decrease in PSA after withdrawal of treatment. Indeed, HF can activate androgen receptor target genes, such as PSA and MMTV-LTR (a reporter gene which expressed androgen-response element), in the presence of ARA70, the first identified androgen receptor co-activator. Yeh et al., *The Lancet*, 349, 852-853 (1997). Because this syndrome often leads to the failure of androgen-ablative therapy, it is desirable to develop better antiandrogens without agonist activity.

The phenolic diarylheptanoid curcumin (1) is the major pigment in turmeric. Curcumin and its analogs show potent anti-oxidant activity, anti-inflammatory activity, Nurfina et al., *Eur. J. Med. Chem.*, 32, 321-328 (1997) cytotoxicity against tumor cells, Syu et al., *J. Nat. Prod.*, 61, 1531-1534 (1998), antitumor-promoting activities, Sugiyama et al., *Biochem. Pharmacol.*, 52, 519-525 (1996). Ruby et al., *Cancer Lett.*, 94, 79-83 (1995) and antiangiogenesis activity (J. L. Arbiser et al. *Mol. Med.* 4: 376 (1998)).

Two cyclic diarylheptanoids, 13-oxomyricanol and myricanone, exhibiting potent antitumor promoting effects on DMBA-initiated and TPA-induced mouse skin carcinogenesis have been reported. Ishida et al., *Cancer Lett.*, 159. 135-140 (2000). In the present study, a number of novel curcumin analogues have been prepared and evaluated for antagonistic activity against the AR in the presence of androgen receptor coactivator, ARA70, using two human prostate cancer cell lines, PC-3 and DU-145. PC-3 cells are androgen-independent tumor cells that do not express functional AR. DU-145 cells are androgen-independent tumor cells that also do not express functional AR.

SUMMARY OF THE INVENTION

According to embodiments of the present invention, the present invention relates to a compound according to formula I:

A first aspect of the present invention is a compound according to formula I or Ia:

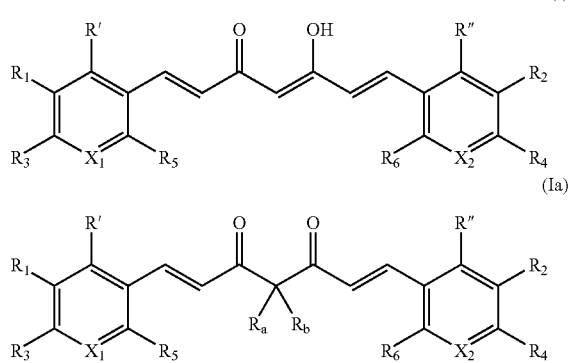

wherein:

R' and R" are each independently selected from the group consisting of H, alkoxy, and halo;

$R_a$ and $R_b$ are each independently selected from the group consisting of H, alkyl and halo;

$R_1$ and $R_2$ are each independently selected from the group consisting of H, hydroxy, alkoxy, nitro, amino, and dialkylamino;

$R_3$ and $R_4$ are each independently selected from the group consisting of H, hydroxy, halo, alkoxy, and —$OR_7C(O)R_8$, wherein $R_7$ is lower alkylene and $R_8$ is alkoxy;

or $R_1$ and $R_3$ together are alkylenedioxy;

or $R_2$ and $R_4$ together are alkylenedioxy;

$R_5$ and $R_6$ are each independently selected from the group consisting of H, halogen, nitro and alkoxy;

$X_1$ is N, or $X_1$ is C bonded to a H, alkoxy or nitro; and $X_2$ is N, or $X_2$ is C bonded to a H, alkoxy or nitro;

subject to the proviso that curcumin is excluded therefrom;

or a pharmaceutically acceptable salt thereof.

A further aspect of the present invention is a compound according to formula II:

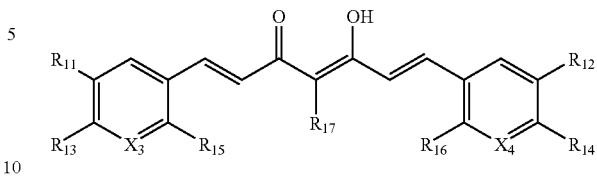

wherein:

$R_{11}$ and $R_{12}$ are each independently selected from the group consisting of alkoxy, nitro, amino, and dialkylamino;

$R_{13}$ and $R_{14}$ are each independently selected from the group consisting of hydroxy, alkoxy, —$OR_{18}C(O)R_{19}$ wherein $R_{18}$ is lower alkylene or alkenylene and $R_{19}$ is alkoxy, and tetrahydropyranyl;

or $R_{11}$ and $R_{13}$ together are alkylenedioxy;

or $R_{12}$ and $R_{14}$ together are alkylenedioxy;

$R_{15}$ and $R_{16}$ are each independently selected from the group consisting of H, halogen, and nitro;

$R_{17}$ is —$R_{20}C(O)OR_{21}$, wherein $R_{20}$ is alkylene or alkenylene and $R_{21}$ is H or alkyl;

$X_3$ is N, or $X_3$ is C bonded to a H, alkoxy or nitro; and $X_4$ is N, or $X_4$ is C bonded to a H, alkoxy or nitro;

or a pharmaceutically acceptable salt thereof.

According to yet other embodiments of the present invention, the present invention relates to compounds according to the formula III:

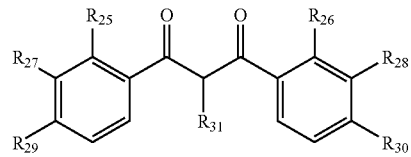

wherein:

$R_{25}$ and $R_{26}$ are each independently H or lower alkyl;

$R_{27}$, $R_{28}$, $R_{29}$ and $R_{30}$ are each alkoxy;

$R_{31}$ is H or lower alkyl;

or a pharmaceutically acceptable salt thereof.

A further aspect of the present invention is a compound of Formula IV:

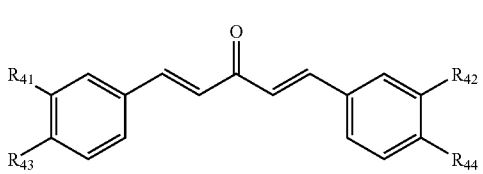

wherein:

$R_{41}$ and $R_{42}$ are each independently hydroxy or alkoxy; and $R_{43}$ and $R_{44}$ are each independently hydroxy or alkoxy;

or a pharmaceutically acceptable salt thereof.

A further aspect of the invention is a compound of the Formula:

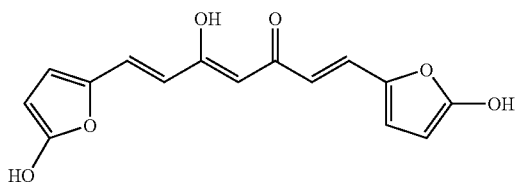

or a pharmaceutically acceptable salt thereof.

According to still other embodiments of the present invention, the present invention relates to a method of treating cancer, comprising administering to a subject in need thereof a treatment effective amount of a compound according to the formulas above or curcumin. Examples of cancers that may be treated include, but are not limited to, skin cancer, small cell lung cancer, testicular cancer, lymphoma, leukemia, esophageal cancer, stomach cancer, colon cancer, breast cancer, endometrial cancer, ovarian cancer, central nervous system cancer, liver cancer and prostate cancer.

According to yet other embodiments of the present invention, the present invention relates to a method of inducing androgen receptor antagonist activity, the method comprising contacting a cancer cell with an androgen receptor antagonist effective amount of a compound according to the formulas above or curcumin.

According to other embodiments of the present invention, the present invention relates to a method of inducing androgen receptor antagonist activity in a subject afflicted with an androgen-related affliction by administering a compound according to the formulas above or curcumin. Examples of androgen-related afflictions include, but are not limited to, baldness, hirsutism, behavioral disorders, acne, and uninhibited spermatogenesis wherein inhibition of spermatogenesis is so desired.

DETAILED DESCRIPTION OF THE INVENTION

Figure 1:
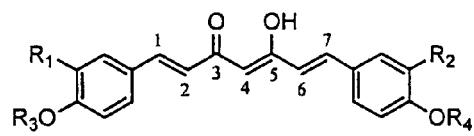
FIG. 1 illustrates structures of curcumin analogues (1-20)
Figure 1:
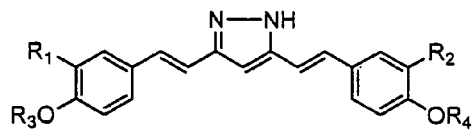
Figure 1:
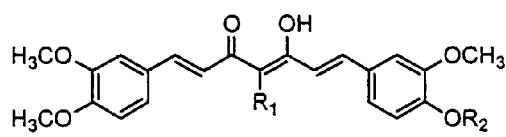
Figure 1:
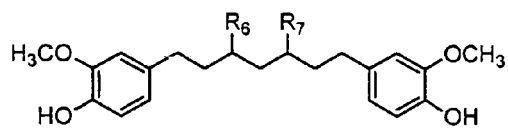
Figure 1:
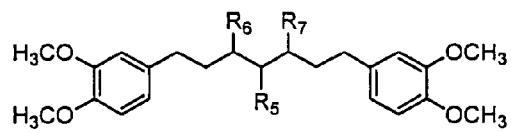
Figure 1:
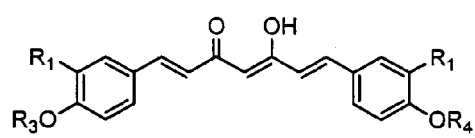

The present invention will now be described more fully hereinafter with reference to the accompanying figures, which further illustrate the invention described herein. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Curcumin" as used herein refers to a compound of the Formula:

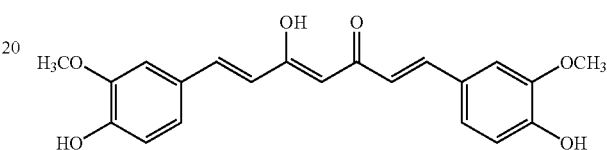

Curcumin, or a pharmaceutically acceptable salt thereof, may be used to carry out the methods described herein.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo. In some embodiments halo is preferably fluoro.

The term "hydroxyalkyl" as used herein refers to C1 to C4 linear or branched hydroxy-substituted alkyl, i.e., —CH$_2$OH, —(CH$_2$)$_2$OH, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —NH$_2$, —NHCH$_3$, —N(CH$_3$)$_2$, etc.

The term "tetrahydropyranyl" refers to a group of the formula:

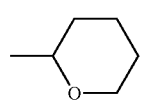

The term "oxyalkyl" as used herein refers to C1 to C4 oxygen-substituted alkyl, i.e., —OCH$_3$, and the term "oxyaryl" as used herein refers to C3 to C10 oxygen-substituted cyclic aromatic groups.

The term "alkylenedioxy" refers to a group of the general formula —ORNO—, —ORNORN—, or —RNORNORN— where each RN is independently alkyl.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

"Androgen" as used herein refers to sex hormones generally known to those skilled in the art and include, but are not limited to, testosterone, dihydrotestosterone, and androstenedione and compounds known to act in mechanisms similar to androgens such as androgen receptor agonists. "Androgen" relates to a hormone or compound, or a combination thereof.

"Antiandrogen withdrawal syndrome" as used herein refers to a phenomenon characterized by either no change or an increase in serum prostate-specific antigen (PSA) concentration upon administration of antiandrogen therapy, and a subsequent decreased PSA concentration observed after withdrawal of antiandrogen therapy.

"Androgen receptor antagonist" as used herein refers to a compound that partially or completely inhibits the activity of an androgen receptor agonist.

"Androgen-related affliction" as used herein refers to conditions wherein an androgen or combination of androgens play a role in the condition observed.

The present invention is concerned primarily with the treatment of human subjects, but may also be employed for the treatment of other animal subjects (i.e., mammals, avians) for veterinary purposes. Mammals are preferred, with humans being particularly preferred.

As noted above, a first aspect of the present invention is a compound according to Formulas I or Ia:

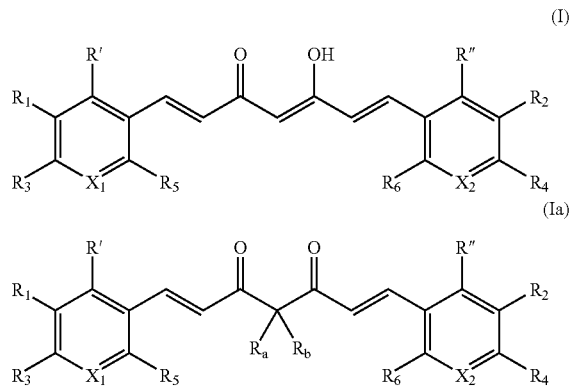

wherein:

R' and R" are each independently selected from the group consisting of H, alkoxy, and halo;

$R_a$ and $R_b$ are each independently selected from the group consisting of H, alkyl and halo;

$R_1$ and $R_2$ are each independently selected from the group consisting of H, hydroxy, alkoxy, nitro, amino, and dialkylamino;

$R_3$ and $R_4$ are each independently selected from the group consisting of H, hydroxy, halo, alkoxy, and —$OR_7C(O)R_8$, wherein $R_7$ is lower alkylene and $R_8$ is alkoxy;

or $R_1$ and $R_3$ together are alkylenedioxy;

or $R_2$ and $R_4$ together are alkylenedioxy;

$R_5$ and $R_6$ are each independently selected from the group consisting of H, halogen, nitro and alkoxy;

$X_1$ is N, or $X_1$ is C bonded to a H, alkoxy or nitro; and $X_2$ is N, or $X_2$ is C bonded to a H, alkoxy or nitro;

subject to the proviso that curcumin is excluded therefrom;

or a pharmaceutically acceptable salt thereof.

In some particular embodiments of compounds of Formulas I and Ia, at least one of R' and R" are alkoxy or halo.

In some particular embodiments of compounds of Formulas I and Ia, $R_a$ is halo and $R_b$ is H, alkyl or halo, preferably alkyl.

In some particular embodiments of comounds of Formulas I and Ia, $R_1$ and $R_2$ are each independently selected from the group consisting of alkoxy, nitro, amino, and dimethylamino.

In some particular embodiments of compounds of Formulas I and Ia, $R_1$ and $R_3$ together are methylenedioxy or ethylenedioxy.

In some particular embodiments of compounds of Formulas I and Ia, $R_2$ and $R_4$ together are methylenedioxy or ethylenedioxy.

In some particular embodiments of compounds of Formulas I and Ia, $R_5$ and $R_6$ are each independently selected from the group consisting of H, F, and nitro.

A further aspect of the present invention is a compound according to Formula II:

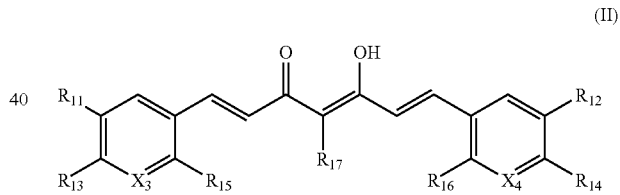

wherein:

$R_{11}$ and $R_{12}$ are each independently selected from the group consisting of alkoxy, nitro, amino, and dialkylamino;

$R_{13}$ and $R_{14}$ are each independently selected from the group consisting of hydroxy, alkoxy, —$OR_{18}C(O)R_{19}$ wherein $R_{18}$ is lower alkylene or alkenylene and $R_{19}$ is alkoxy, and tetrahydropyranyl;

or $R_{11}$ and $R_{13}$ together are alkylenedioxy;

or $R_{12}$ and $R_{14}$ together are alkylenedioxy;

$R_{15}$ and $R_{16}$ are each independently selected from the group consisting of H, halogen, and nitro;

$R_{17}$ is —$R_{20}C(O)OR_{21}$, wherein $R_{20}$ is alkylene or alkenylene and $R_{21}$ is H or alkyl;

$X_3$ is N, or $X_3$ is C bonded to a H, alkoxy or nitro; and $X_4$ is N, or $X_4$ is C bonded to a H, alkoxy or nitro;

or a pharmaceutically acceptable salt thereof.

In some particular embodiments of compounds of Formula II, $R_{20}$ is alkenylene.

In some particular embodiments of compounds of Formula II, $R_{13}$ and $R_{14}$ are tetrahydropyranyl.

In some particular embodiments of compounds of Formula II, $R_{11}$ and $R_{12}$ are each independently selected from the group consisting of alkoxy, nitro, amino, and dimethylamino.

In some particular embodiments of compounds of Formula II, $R_{11}$ and $R_{13}$ together are methylenedioxy or ethylenedioxy.

In some particular embodiments of compounds of Formula II, $R_{12}$ and $R_{14}$ together are methylenedioxy or ethylenedioxy.

In some particular embodiments of compounds of Formula II, $R_{15}$ and $R_{16}$ are each independently selected from the group consisting of H, F, and nitro.

According to yet other embodiments of the present invention, the present invention relates to compounds according to the formula III:

(III)

wherein:
$R_{25}$ and $R_{26}$ are each independently H or lower alkyl;
$R_{27}$, $R_{28}$, $R_{29}$ and $R_{30}$ are each alkoxy;
$R_{31}$ is H or lower alkyl;
or a pharmaceutically acceptable salt thereof.

A further aspect of the present invention is a compound of Formula IV:

(IV)

wherein:
$R_{41}$ and $P_{42}$ are each independently hydroxy or alkoxy; and
$R_{43}$ and $R_{44}$ are each independently hydroxy or alkoxy;

or a pharmaceutically acceptable salt thereof.

A further aspect of the invention is a compound of the Formula:

or a pharmaceutically acceptable salt thereof.

A. Specific compounds

Specific compounds within the scope of the present invention include, but are not limited to:

S-1

S-2

S-3

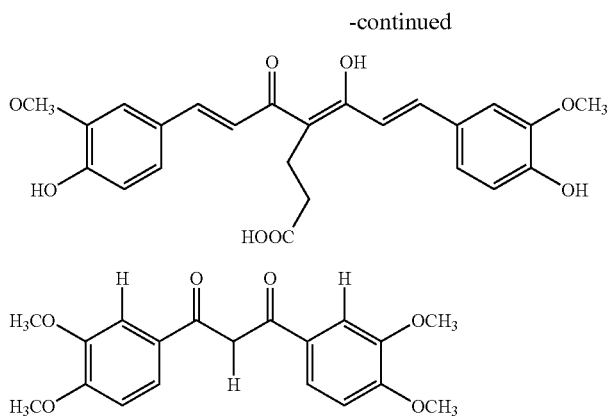

Additional examples of compounds of the invention are set forth below.

B. Synthesis of Compounds

Variations on the following general synthetic methods will be readily apparent to those skilled in the art and are deemed to be within the scope of the present invention.

Figure 2:
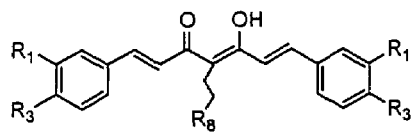
FIG. 2 illustrates structures if curcumin analogues (21-44)
Figure 2:
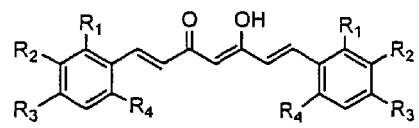
Figure 2:
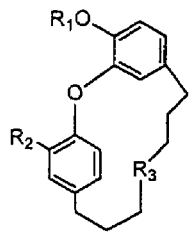
Figure 2:
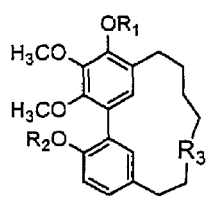
Figure 2:
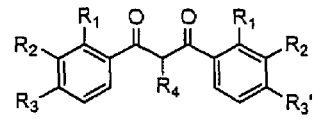

FIGS. 1 and 2 show the structures of curcumin analogues and 1,3-diaryl-1,3-diketopropane derivatives. Curcumin (1), demethoxycurcumin (2) and bisdemethoxycurcumin (3) were obtained by column chromatography (silica gel, $CHCl_3$-MeOH) of commercially available curcumin (Aldrich), which contained 2 and 3 as minor components. Treatment of 1 with diazomethane gave dimethylated curcumin (4) and monomethylated curcumin (9). Methylation of 1 with methyl iodide and $K_2CO_3$ furnished the trimethylated derivative 10, in which a methyl group was also introduced at the C-4 position. Compounds 58 were synthesized by heating 1-4 with histidine hydrazide, AcOH and p-TsOH overnight. Hydrogenation of 1 with 10% Pd—C gave a mixture of 11-13. Similarly, compounds 14-16 and 17-18 were obtained by hydrogenation of 4, and 10, respectively. Heating 1 with methyl chloroacetate, NaI and $K_2CO_3$ in acetone furnished a mixture of monomethoxycarbonylmethyl ether 18 and bis-methoxycarbonylmethyl ether 19, which were separated by preparative TLC (PLC). Compounds 21-23 were prepared from benzene or vanillin and ethyl 4-acetyl-5-oxohexanoate by a method known in the art. Pedersen et al., *Liebigs Ann. Chem.*, 1557-1569 (1985). Compounds 21-23 constitute an unseparable mixture of keto-enol tautomeric isomers. The syntheses of 24-38 were described in our previous paper. Ishida et al., *Cancer Lett.*, 159. 135-140 (2000). Ishida et al., Synthesis and Evaluation of Curcumin Analogues as Cytotoxic Agents. Unpublished data. Compounds 39-44 were purchased from Aldrich, Inc (Milwaukee, Wis.).

C. Pharmaceutically Acceptable Salts

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

D. Pharmaceutical Formulations

Curcumin and the curcumin analogues of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\ris buffer (pH 6) or ethanol/water and contain from 0.01 to 0.2M active ingredient.

E. Methods of Use

In addition to the compounds of the formulas described herein, the present invention also provides useful therapeutic methods. For example, the present invention provides a method of inducing cytotoxicity against tumor cells, antitumor-promoting activities, anti-inflammatory activity. More specifically, the present invention provides a method of inducing androgen receptor antagonist activity. The androgen receptor antagonist activity is a useful means of inhibiting androgen related tumor or cancer cell growth.

Cancer cells which may be inhibited include cells from skin cancer, small cell lung cancer, testicular cancer, lymphoma, leukemia, esophageal cancer, stomach cancer, colon cancer, breast cancer, endometrial cancer, ovarian cancer, central nervous system cancer, liver cancer and prostate cancer.

The present invention also provides a method of treating cancer in a subject afflicted with cancer. These subjects also include subjects afflicted with antiandrogen withdrawal syndrome. The method includes administering to the subject in an effective cancer-treating amount a compound of the formulas of the present invention. The method is useful for the treatment of a variety of cancer cells which include but are not limited to skin cancer, small cell lung cancer, testicular cancer, lymphoma, leukemia, esophageal cancer, stomach cancer, colon cancer, breast cancer, ovarian cancer, central nervous system cancer, liver cancer and prostate cancer.

Compounds with anti-androgen activity also have the potential to be therapeutically useful for treatment of androgen-potentiated hair disorders such as baldness and hirsutism. Anti-androgenic compounds may also be therapeutically useful as a form of male contraception where it is generally known and understood by those skilled in the art that androgens are required to maintain spermatogenesis. Additionally, compounds with anti-androgenic activity may be useful for the treatment of behavioral disorders which include, but are not limited to, aggressiveness, violent behavior and sexual aggression. Anti-androgenic compounds may also be therapeutically useful for the treatment of acne due to the altered levels of hormones, including androgens, associated with acne disorders.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

A. Materials and Methods

Compounds 1-3 were obtained by column chromatography (silica gel, $CHCl_3$-MeOH) of commercially available curcumin (Aldrich), which contained 2 and 3 as minor components. Compounds 39-44 were purchased from Aldrich, Inc (Milwaukee, Wis.).

Dimethylcurcumin (4). Curcumin (1) in $Et_2O$ and MeOH was treated with excess of diazomethane in ether for 24 h. The solvents were removed in vacuo and the residue was purified by silica gel column chromatography and PLC to yield yellow needles of 4 (yield 19.8%); mp 129-130° C. (MeOH) (Roughley et al., *J. Chem. Soc. Perkin I*, 2379-2388 (1973))(128-130° C.); $^1$H NMR (300 MHz, CDCl$_3$): δ 3.93 (12H, s, OCH$_3$×4), 5.82 (1H, s, 1-H), 6.48 (2H, d, 16 Hz), 6.88 (2H, d, J=8 Hz), 7.08 (2H, bs), 7.15 (2H, bd), 7.61 (2H, J=16 Hz); $^{13}$CNMR (300 MHz, CDCl$_3$): δ 55.9, 56.0, 101.3, 109.8, 111.1, 122.0, 122.6, 128.1, 140.4, 149.2, 151.0, 183.2.

Preparation of pyrazol derivative (8). To a solution of 1-4 in butanol and ethanol were added histidine hydrazide (1 equiv.), acetic acid and p-TsOH. The solution was refluxed for 24 h, and then the solvent was removed in vacuo. The residue was purified by silica gel column chromatography and PLC.

Compound 8. Yellow powder (yield 17.5%), mp 166-168° C. (MeOH); $^1$H NMR (300 MHz, CDCl 3): δ 3.92 (6H, s, OCH$_3$×2), 3.94 (6H, s, OCH$_3$×2), 6.62 (1H, s, 1-H), 6.86 (2H, d, J=8 Hz), 6.93 (2H, d, J=16 Hz), 7.04 (2H, dd, J=8, 2 Hz), 7.06 (2H, bs), 7.05 (2H, d, J=16 Hz); $^{13}$CNMR (300 MHz, CDCl$_3$): δ 55.8, 55.9, 99.6, 108.6, 111.2, 115.8, 120.1, 129.7, 130.6, 149.1, 149.3; Anal. calcd. for C$_{23}$H$_{24}$N$_2$O$_4$·¼H$_2$O: Theory: C, 66.57; H, 6.44; N, 6.75. Found C, 66.44; H, 6.19; N, 6.27.

Monomethylcurcumin (9). Curcumin (1) in MeOH was treated with excess diazomethane in Et$_2$O for 24 h. After removal of solvents, the residue was purified by silica gel column chromatography and PLC to yield a yellow amorphous solid (yield 20%); mp 89-91° C., [α]$_D$ –3.6 (c=1.14, CHCl$_3$); $^1$H NMR (300 MHz, CDCl$_3$): δ 3.93 (9H, s, OCH$_3$×3), 5.81 (1H, s, 1-H), 5.94 (1H, bs, OH), 6.49 (2 H, bd, J=15 Hz), 6.93 (1H, d, J=8 Hz), 6.97 (1H, d, J=8 Hz), 7.10 (4H, m), 7.60 (2 H, bd, J=15 Hz); EIMS m/z 382 (M*), HRFABMS 382.1396 (M+H$^+$) (calcd for C$_{22}$H$_{22}$O$_6$: 382.1416).

Hydrogenation of 1, 4 and 10 (11-18). A solution of starting material in EtOAc was shaken with 10% Pd—C under H$_2$ (45 psi) overnight using a Parr's apparatus. The solution was filtered and concentrated in vacuo to give a residue, which was purified by silica gel column chromatography and PLC.

Tetrahydrocurcumin (11). White powder, mp 92-93° C. (Roughley et al., *J. Chem. Soc. Perkin I*, 2379-2388 (1973), 95-96° C.), $^1$H NMR (300 MHz, CDCl$_3$): δ 2.53-2.58 (3H, m), 2.78-2.88 (5H, m), 3.87 (6H, s, OCH$_3$×2), 5.43 (1H, s, 1-H), 5.50 (2H, s, ArOH), 6.65 (2H, d, J=8 Hz), 6.69 (2H, s), 6.83 (2H, d, J=8 Hz); $^{13}$CNMR (300 MHz, CDCl$_3$): δ 31.3, 40.4, 55.8, 99.8, 111.0, 114.3, 120.8, 132.6, 144.0, 146.4 and 193.2.

Hexahydrocurcumin (12). White powder, mp 87-88° C. (Roughley, P. J. et al., *J. Chem. Soc. Perkin I*, 2379-2388 (1973), 78-80° C.), $^1$H NMR (300 MHz, CDCl$_3$): δ 1.60-1.81 (2H, m), 2.53-2.97 (8H, m), 3.85 (6H, s, OCH$_3$×2), 4.06 (1H, m, 2-H), 6.70 (4H, m), 6.80 (2H, d, J=8 Hz); $^{13}$CNMR (300 MHz, CDCl 3): δ 29.7, 31.7, 38.8, 45.8, 49.8, 56.3, 67.4, 111.5, 111.6, 114.8, 114.9, 121.2, 121.4, 133.0, 134.2, 144.2, 144.5, 146.9, 147.9 and 211.9.

Octahydrocurcumin (13). Colorless oil, $^1$H NMR (300 MHz, CDCl$_3$): δ 1.61 (2H, m), 1.75 (4H, m), 2.53-2.70 (4H, m), 3.80 (6H, s, OCH$_3$×2), 3.91 (2H, brs), 6.13 (2H, s, ArOH), 6.65 (2H, d, J=8 Hz), 6.69 (2H, bs) 6.82 (2H, bd, J=8 Hz), $^{13}$CNMR (300 MHz, acetone-d$_6$): δ 31.1, 39.8, 42.6, 35.6, 72.0, 111.0, 114.3, 120.6, 133.6, 143.6 and 146.4.

Compound 14. White powder (yield 26.0%), mp 60-61° C., $^1$H NMR (300 MHz, CDCl$_3$): δ 2.56 (3H, m), 2.86 (5H, m), 3.85 (12H, s, OCH$_3$×4), 5.44 (1H, s, 1-H), 6.71 (4H, m), 6.78 (2H, bd); Anal. calcd. for C$_{23}$H$_{28}$O$_6$·¼H$_2$O: Theory: C 68.21; H, 7.09. Found C, 68.25; H, 7.06.

Compound 15. White powder (yield 20.0%), mp 94-95° C., $^1$H NMR (300 MHz, CDCl$_3$): δ 1.65-1.80 (2H, m), 2.53-2.84 (8H, m), 3.85 (12H, s, OCH$_3$×4), 4.05(1H, bs, 2'-H), 6.68-7.23 (4H, m), 6.79 (2H, bd), Anal. calcd. for C$_{23}$H$_{30}$O$_6$·¼H$_2$O: Theory: C, 67.88; H, 7.55. Found C, 67.73; H, 7.49.

Compound 16. Colorless oil (yield 4.2%), mp 60-61° C., $^1$H NMR (300 MHz, CDCl$_3$): δ 1.55-1.65 (4H, m), 1.73-1.82 (3H, m), 2.60-2.72 (3H, m), 3.86 (6H, s, OCH$_3$×2), 3.87 (8H, bs, OCH$_3$×2, 2,2'-H), 6.72-6.78 (4H, m), 6.79 (2H, bd), 7.27(2H, s, OH×2), EIMS m/z: 404 (M$^+$), HRFAB-MS m/z 404.219070 (M+H)$^+$ (calcd for C$_{23}$H$_{32}$O$_6$: 404.2198891).

Compound 17. Colorless oil (yield 5.9%), $^1$H NMR (300 MHz, CDCl$_3$): δ 1.10 (3H, d), 1.80 (1H, m), 2.43-2.82 (8H, m), 3.86 (6H, s, OCH$_3$×2), 3.87 (6H, s, OCH$_3$×2), 3.94 (1H, bs, 2'-H)* 0.70-6.78 (6H, m), EIMS m/z 416(M$^+$).

Compound 18. Colorless oil (yield 6.95%), $^1$H NMR (300 MHz, CDCl$_3$): δ 0.95 (3H, d, 1-CH$_3$), 1.52 (1H, m), 1.84 (2H, m), 2.67 (6H, m), 3.83 (14H, bs, OCH$_3$×4, 2, 2'-H), 6.78 (6H, m); EIMS m/z: 418 (M$^+$), HRFAB-MS m/z 418.236618 (M+H)$^+$(calcd for C$_{24}$H$_{34}$O$_6$: 418.2355392).

Preparation of 19 and 20. A mixture of curcumin (1, 100 mg, 0.81 mmol) in acetone (20 mL) with methylchloroacetate (2 mL) and NaI (20 mg) was refluxed with anhydrous potassium carbonate (176 mg) for 24 h with stirring. After filtration and removal of solvent, the residue was purified by silica gel column chromatography to yield the corresponding methyl acetates 19 and 20.

Compound 19: Yellow powder (yield 20.0%), mp 60-61° C., mp 66-67° C., [α]$_D$ –2.4 (c=2.08, CHCl$_3$); $^1$H NMR (300 MHz, acetone-d$_6$): δ 3.73 (3H, s, —COOC$\underline{H}_3$), 3.86 (6H, s, OC$\underline{H}_3$×2), 4.79 (2H, s, O—C$\underline{H}_2$—COO), 5.99 (1H, s, 1-H), 6.70 and 6.73 (both 1H, d, J=15.3 Hz), 6.88 (1H, d, J=8 Hz), 6.94 (1H, d, J=8 Hz), 7.17 (2H, m), 7.33 (2H, m), 7.59 and 7.61 (both 1H, d, J=15.3 Hz), $^{13}$CNMR (300 MHz, CDCl$_3$): d 51.8, 55.9, 55.9, 65.9, 101.4, 111.2, 111.6, 114.3, 115.9, 121.8, 122.6, 123.0, 123.5, 127.6, 128.7, 129.8, 140.3, 141.3, 148.4, 149.8, 150.0, 150.4, 169.4, 183.4, 184.6; Anal. calcd. for C$_{24}$H$_{24}$O$_8$·¾H$_2$O: Theory: C, 63.50; H, 5.66. Found C, 63.53; H, 5.65.

Compound 20: Yellow powder (yield 20.0%), mp 141-142° C. (MeOH), [α]$_D$ –0.29 (c=5.86, CHCl$_3$); $^1$H NMR (300 MHz, CDCl$_3$): δ 3.80 (6H, s), 3.93 (6H, s), 4.73 (4H, s, O—C$\underline{H}_2$—COO×2), 5.82 (1H, s, 1-H), 6.50 (2H, d, J=16 Hz), 6.79 (2H, d, J=8 Hz), 7.09 (4H, bs), 7.58 (2H, d, J=16 Hz), $^{13}$C NMR (300 MHz, CDCl$_3$): d 52.3, 56.0, 66.0, 101.4, 110.7, 113.6, 122.0, 122.7, 129.5, 140.1, 149.0, 149.7, 169.0, 183.1; Anal. calcd. for C$_{27}$H$_{28}$O$_{10}$·½H$_2$O: Theory: C, 62.18; H, 5.60. Found C, 62.31; H, 5.57.

Compound 21: Yellow amorphous solid (yield 3.0%), $^1$H NMR (300 MHz, CDCl 3): δ 2.58 (2H, m), 2.95 (2H, m), 7.12 (2H, d, J=15 Hz), 7.40 (6H, m), 7.60 (4H, m), 7.81(2H, d, J=15 Hz), 12.65(1H, bs); Anal. calcd. for C$_{22}$H$_{20}$O$_4$: Theory: C, 75.84, H, 5.79. Found C, 75.56, H, 5.74.

Compound 22: Yellow amorphous solid (yield 25.0%), Anal. calcd. for C$_{26}$H$_{28}$O$_8$: Theory: C, 66.66, H, 6.02. Found C, 66.38, H, 6.16.

Compound 23: Yellow powder (yield 45.0%), mp 144-146° C. (MeOH) (Pedersen et al., *Liebigs Ann. Chem.* 1557-1569 (1985), 71-73° C. (CH$_2$Cl$_2$)) Anal. calcd. for C$_{24}$H$_{26}$O$_8$·2·½H$_2$O: Theory: C, 59.87; H, 5.23. Found C, 59.94; H, 5.11.

The structures of 1-4, 10-13, 22, and 23 were confirmed by comparison of their physical spectral data with those reported in the literature. Pedersen et al., *Liebigs Ann. Chem.* 1557-1569 (1985), Roughley et al., *J. Chem. Soc. Perkin I*, 2379-2388 (1973).

B. Suppression of DHT-Mediated Transcription Activity.

Cell Culture and Transfections. Human prostate cancer DU145 and PC-3 cells were maintained in Dulbecco's minimum essential medium (DMEM) containing penicillin (25 units/mL), streptomycin (25 μg/mL), and 10% fetal calf serum (FCS). For AR transactivation assay, PC-3 cells were transfected with an AR expression plasmid and reporter gene. Because of a low content of endogenous AR coactivators, DU-145 cells were transfected with expression plasmids for AR and ARA70, and reporter gene. The conditions were followed as previously described in Miyamoto et al., Proc. Natl. Acad. Sci. USA, 95, 7379-7384 (1998), with minor modifications.

Transfections were performed using the SuperFect kit according to manufacturer's procedures (Qiagen, Chatsworth, Calif.). Briefly, $1\times10^5$ cells were plated on 35-mm dishes 24 h before transfection, and then a reporter plasmid, MMTV-Luciferase, which contains MMTV-LTR promoter and AR-binding element, was co-transfected with an AR expression plasmid (wild type or mutant), or pSG5ARA70. PRL-TK was used as an internal control for transfection efficiency. The total amount of DNA was adjusted to 3.0 g with pSG5 in all transcriptional activation assays. After a 2 h transfection, the medium was changed to DMEM-10% charcoal stripped serum medium, and 14-16 h later, the cells were treated with DHT, antiandrogen, or test compounds. After another 14-16 h, the cells were harvested and tested for luciferase activity in luciferase assays (Promega, Dual Luciferase Assay System, Madison, Wis.). Data were expressed in relative luciferase activity as compared to an internal luciferase positive control.

C. Results and Discussion

The aim of this work was to investigate novel curcumin analogues for antiandrogen receptor antagonist activity. The synthesis and evaluation of novel curcumin analogues as antiandrogen receptor antagonists and antitumor agents are reported herein.

Figure 3A:
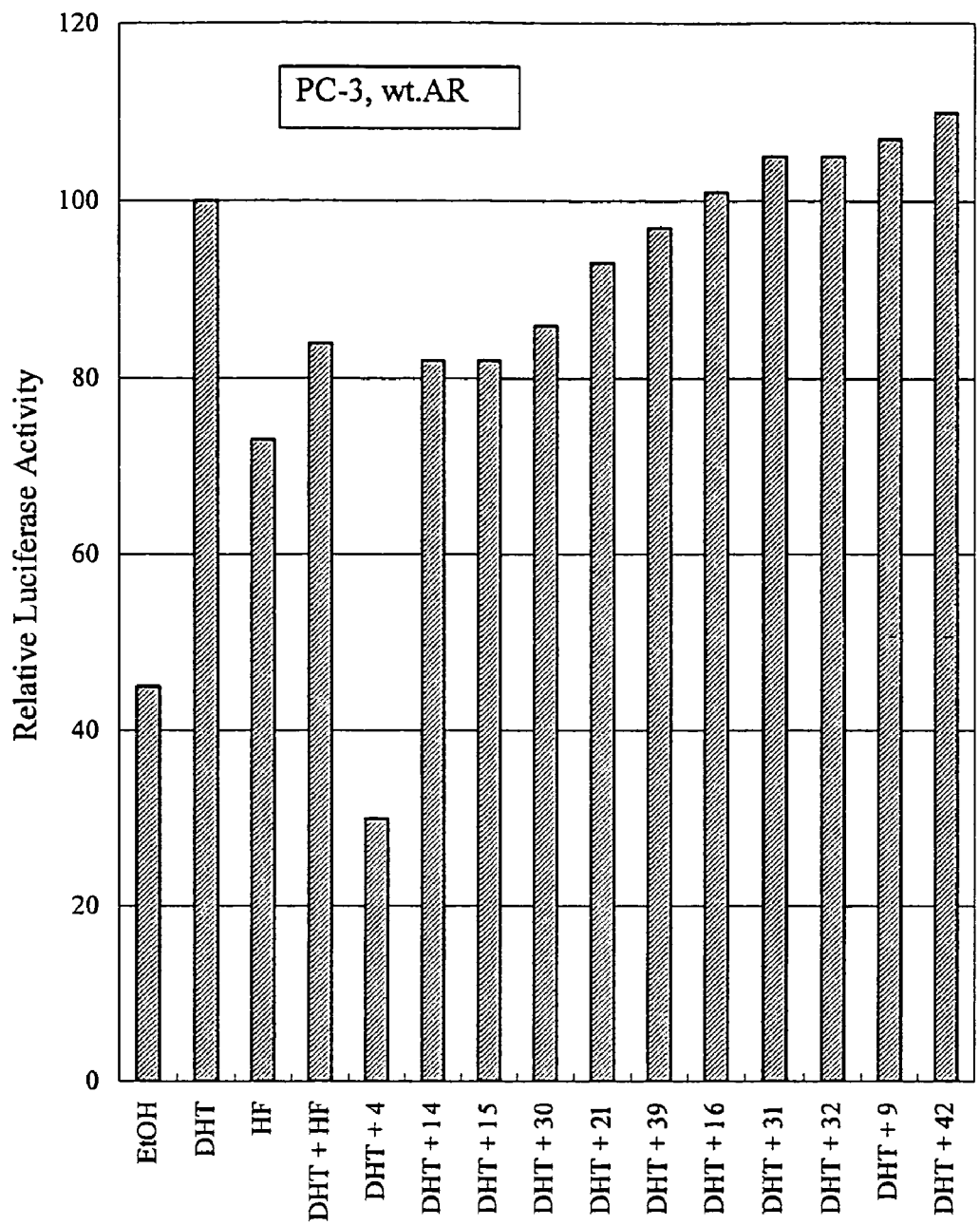
FIG. 3A illustrates suppression of DHT-mediated MMTV transcription AR activity by hydroxyflutamide (HF) and selected compounds.
Figure 3B:
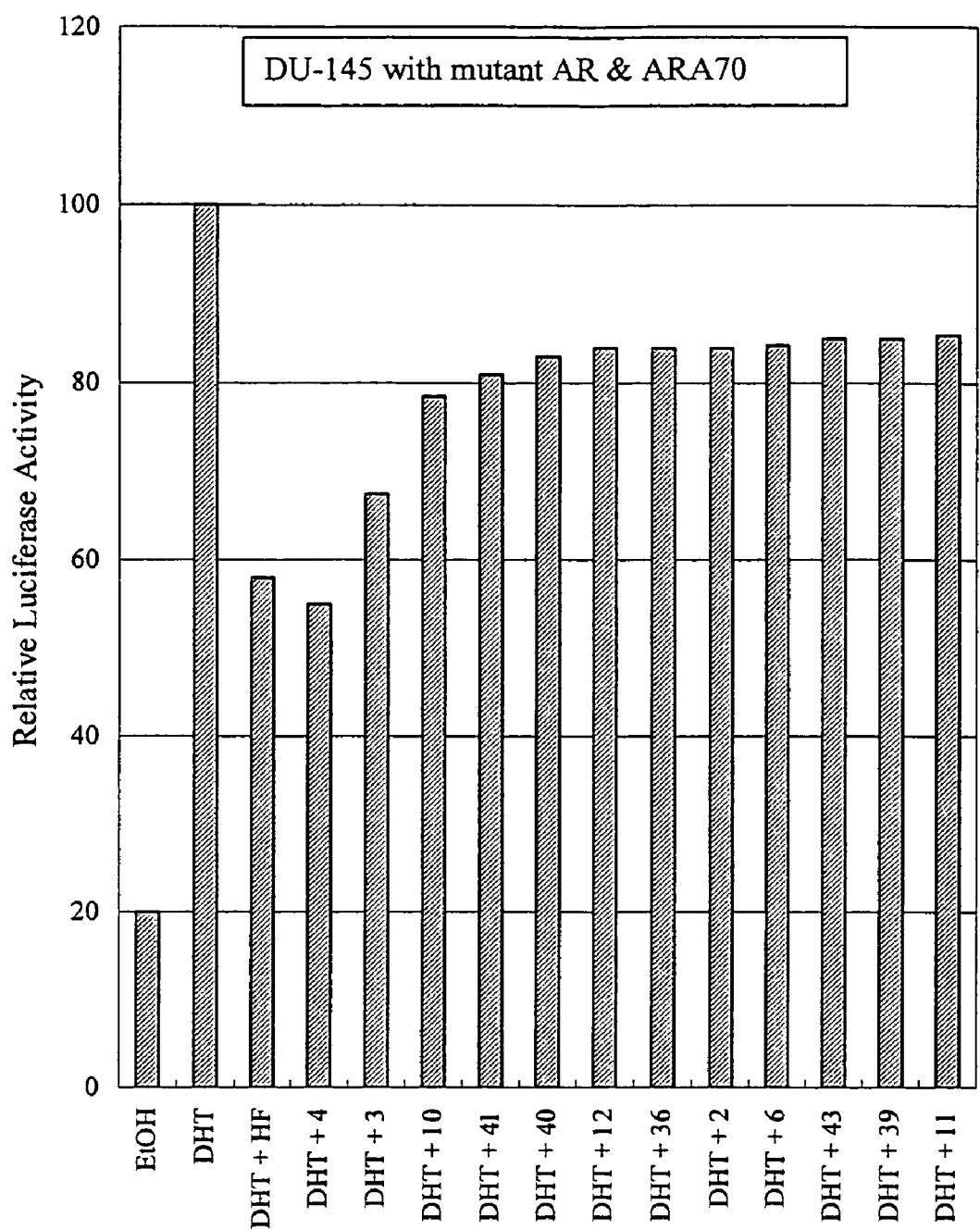
FIG. 3B illustrates suppression of DHT-mediated MMTV transcription AR activity by hydroxyflutamide (HF) and selected compounds.
Figure 3C:
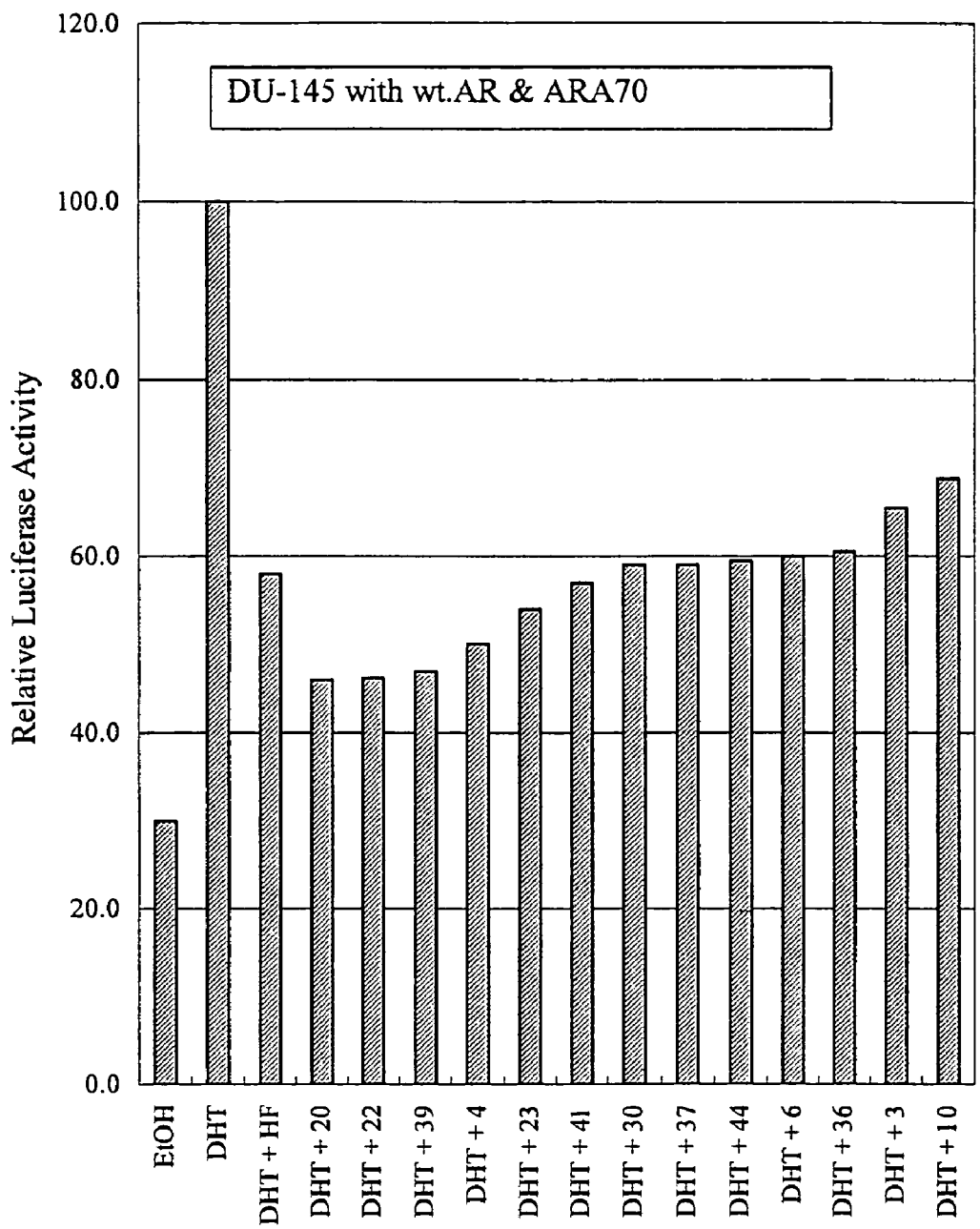
FIG. 3C illustrates suppression of DHT-mediated MMTV transcription AR activity by hydroxyflutamide (HF) and selected compounds.

Forty-seven curcumin derivatives (1-47) were tested for antagonistic activity against the AR using two different human prostate cancer cells, PC-3 and DU-145 (FIGS. 3A-C). The parental compound, curcumin (1), was inactive in all cases. However, dimethylated curcumin (4) showed significant antagonistic activity (reducing 70% of DHT-induced AR activity) when assayed in PC-3 cells transfected with wild-type AR and was more potent than HF (which reduced 16% of DHT-induced AR activity, FIG. 3A). Compound 4 also showed the highest antagonist activity when assayed in DU-145 cells transfected with a mutant LNCaP AR and ARA70 (showing a 45% reduction in DHT-induced AR activity, FIG. 3B), indicating that compound 4 is an effective antagonist for both normal and mutant AR.

To determine the structural requirements for AR antagonist activity in this series of compounds, a structure-activity relationship (SAR) study was conducted in a PC-3 cell assay system. Compared with 4, monomethylated curcumin (9) lacks one O-methyl groups at the p-position on one benzene ring, and was significantly less active than 4 (FIG. 3B). Thus, the bis(3,4-dimethoxyphenyl) groups of 4 are important to the activity. Introducing a methyl group at C-4 of 4 (10) resulted in decreased activity (FIG. 3B). Compounds 14 and 15, which were obtained by hydrogenation of 4, were as potent as HF with an 18% reduction in DHT-induced AR activity, but were considerably less active compared to 4 (FIG. 3A). Converting the β-diketone moiety of 4 to the corresponding pyrazol derivative 8 greatly reduced the activity. Furthermore, 1,3-bis(3,4-dimethoxyphenyl)-1,3-propandione (39), which contains the bis-aryl groups found in 4 but lacks the conjugated double bonds, was less active than 4 (FIGS. 3A and 3B), indicating that the conjugated double bonds also contribute to the activity of 4. These observations suggested that the bis(3,4-dimethoxyphenyl) groups and the conjugated β-diketone moiety are crucial for the activity.

Data in FIG. 3C show a somewhat different cell assay system where antiandrogen activity was assayed in DU-145 cells transfected with wild-type AR and ARA70. Compounds 4, 20, 22, 23, and 39 showed comparable or more potent antiandrogen activity than HF in this assay system. Compounds 20 and 22 were almost equipotent (54% and 53.8% reduction, respectively) and were slightly more active than 4 (49.9%). Because curcumin (1) itself was not active, introducing either methoxycarbonylmethyl groups at the phenolic hydroxyls (20) or an ethoxycarbonylethyl group at C-4 (22) greatly contributed to the anti-AR activity in DU-145 cells in the presence of wild-type AR and ARA70.

In this study, we also examined the antiandrogen activity of fluorodiarylheptanoids 24-29 and cyclic diarylheptanoids 30-38. Compounds 24-29 have fluorine or trifluoromethyl substituents on both benzene rings, but showed weak activity or were inactive. Among the cyclic diarylheptanoids 30-38, compound 30 was the most active and was almost as active as HF (FIGS. 3A and 3C). The remaining cyclic diarylheptanoids showed weak antagonistic activity.

In conclusion, we have prepared a number of curcumin analogues and evaluated their potential antiandrogen activity in three different assay conditions using human prostate cancer cell lines. Compounds 4 showed promising antiandrogen activities in all assays. Compounds 4, 20, 22, 23 and 39 have been identified as a new class of antiandrogen agents. The SAR study revealed that bis(3,4-dimethoxyphenyl) moieties, a conjugated β-diketone, and an ethoxycarbonylethyl group at the C-4 position play important roles in the antagonistic activity.

EXAMPLE 2

Synthesis and Characterization of Additional Curcumin Analogs

Additional curcumin analogs are shown in Table 1 below.

TABLE 1

Curcumin analogues.

| Compound | Structure |
|---|---|
| LL-7 | 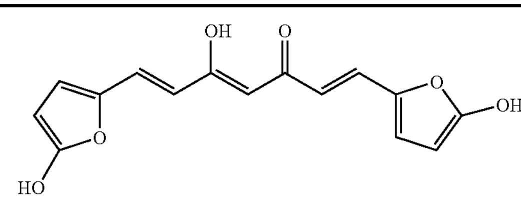 |

TABLE 1-continued

Curcumin analogues.

| Compound | Structure |
|---|---|
| LL-10 | 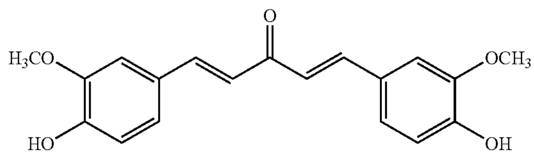 |
| LL-17 | 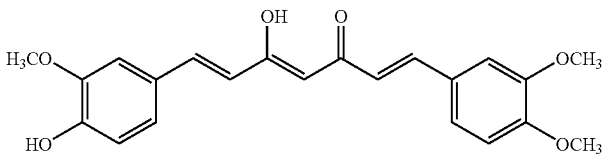 |
| LL-18 | 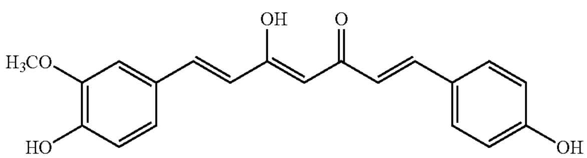 |
| LL-27-B | 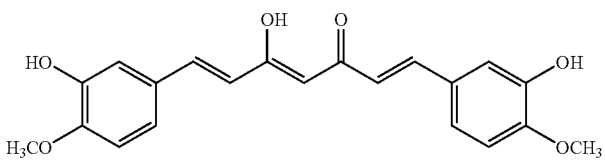 |
| LL-32-B | 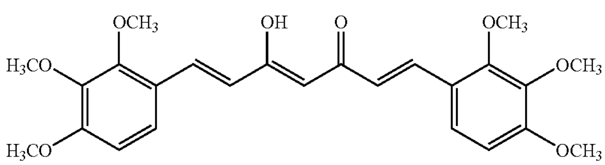 |
| LL-35 | 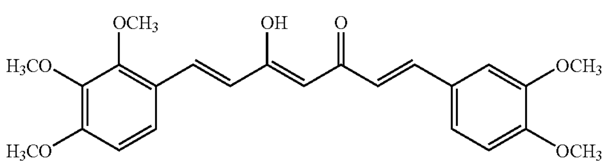 |
| LL-36 | 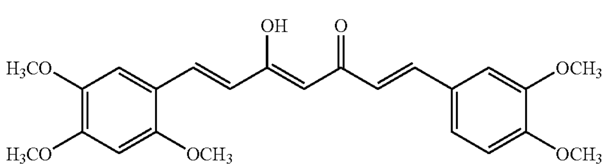 |
| LL-41 | 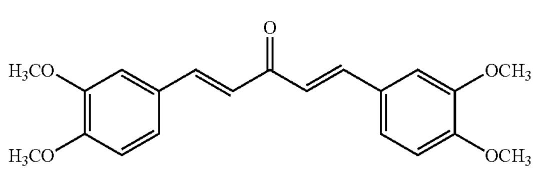 |

TABLE 1-continued
Curcumin analogues.
| Compound | Structure |
| --- | --- |
| LL-46 | 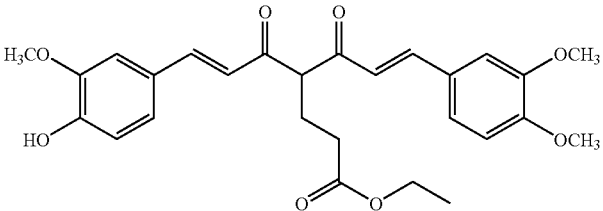 |
| LL-55 | 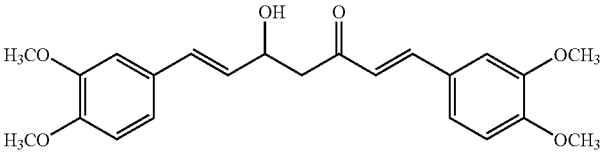 |
| LL-61 | 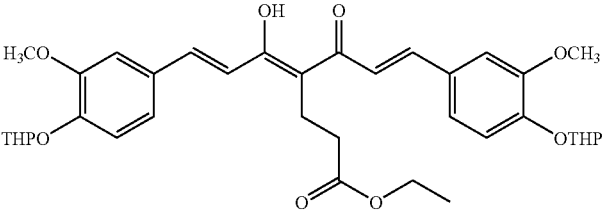 |
| LL-62 | 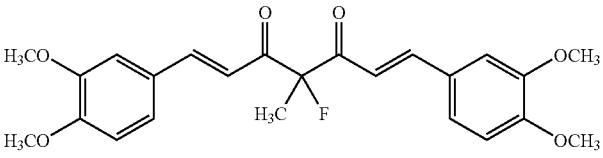 |
| LL-65 | 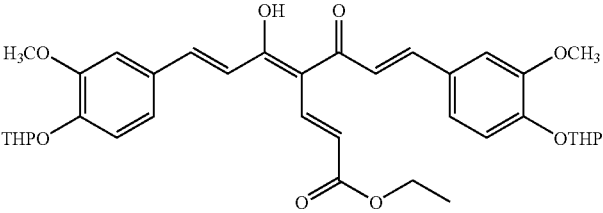 |
| LL-66 | 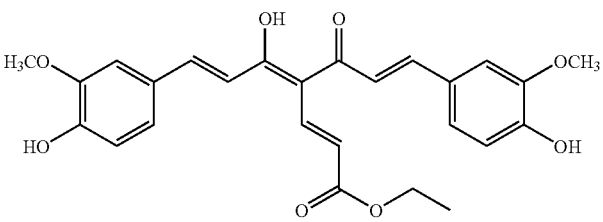 |
| LL-80 | 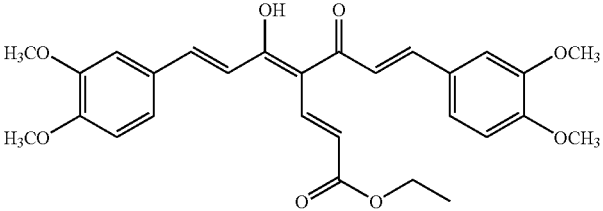 |

TABLE 1-continued

Curcumin analogues.

| Compound | Structure |
|---|---|
| HOJ-7 | 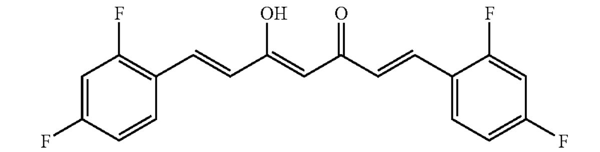 |
| HOJ-9 | 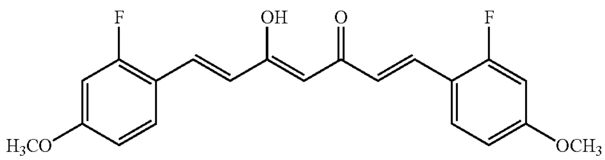 |
| HOJ-10 | 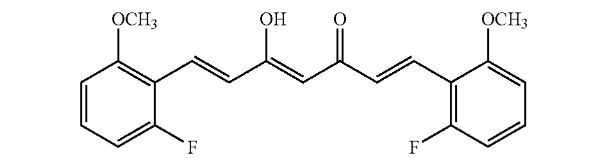 |

The foregoing compounds are synthesized as follows:

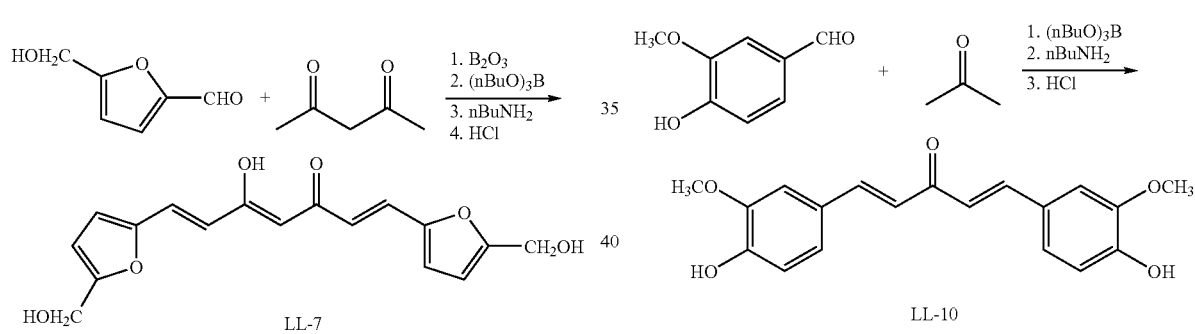

LL-7: The synthetic method was modified from the strategy developed by Pedersen et al. Acetylacetone (0.2 ml, 2 mmol) and boric anhydride (100 mg, 1.4 mmol) were dissolved in 15 ml of ethyl acetate. The solution was stirred at 70° C. for 0.5 hour. 5-hydroxymethylfuran (506 mg, 4 mmol) and tributyl borate (1.08 ml, 4 mmol) were added. The mixture was stirred for 30 min. Then butylamine (0.3 ml, 3 mmol) dissolved in 4 ml of EtOAc was added dropwise during 15 min. The stirring continued for 5 hours at 85° C. The mixture was then hydrolyzed by adding 8 ml of 1N HCl and stirring for 0.5 hour at 60° C. The organic layer was separated. The aqueous layer was extracted with ethyl acetate. The combined organic layers were washed until neutral, dried with anhydrous sodium sulphate. The solven was removed in vacu. The crude products were purified by CombiFlash® column chromatography eluting with hexane-EtOAc. 68 mg red powder was obtained in 12% yield. $^1$H NMR (300 MHz, CDCl$_3$): δ 4.67 (4H, s), 5.74 (H, s), 6.40 (2H, d, J=3.3 Hz), 6.53 (2H, d, J=15.3 Hz), 6.58 (2H, d, J=3.3 Hz), 7.43 (2H, d, J=15.6 Hz).

LL-10: vanillin (1.52 g, 10 mmol) and tributyl borate (2.7 ml, 10 mmol) were dissolved in 8 ml ethyl acetate. To the stirring solution, acetone (0.37 ml, 5 mmol) was added. The solution was stirring for 10 min. Butylamine (1 ml, 10 mmol) in 5 ml EA was added dropwise. The solution was stirring for hours at 50° C. 7 ml of 1N HCl was added. The mixture was stirring for 0.5 hour at 50° C. $^1$H NMR (300 MHz, CDCl$_3$): δ 3.94 (6H, s), 6.90 (2H, d, J=8.4 Hz), 6.95 (2H, d, J=15.6 Hz), 7.11 (2H, d, J=1.8 Hz), 7.20 (2H, dd, J=1.8 Hz, J=8.4 Hz), 7.68 (2H,d, J=15.6 Hz).

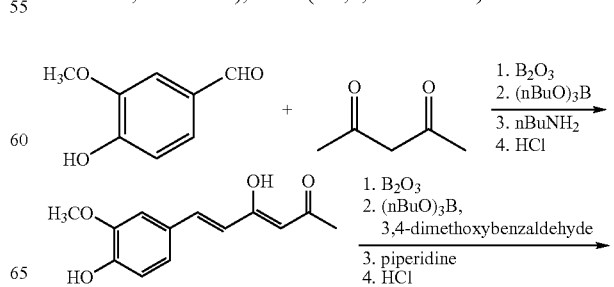

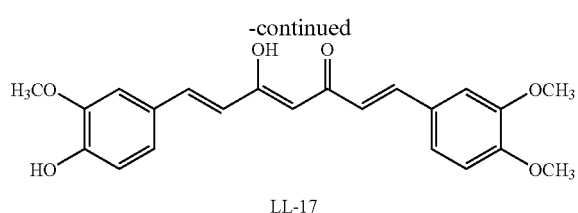

LL-17

LL-1: Acetylacetone (3.1 ml, 30 mmol) and boric anhydride (1.5 g, 21 mmol) were dissolved in 20 ml of ethyl acetate. The solution was stirred at 70° C. for 1 hour. To the solution vanillin (1.52 g, 10 mmol) and tributyl borate (2.7 ml, 10 mmol) were added. The mixture was stirred for 30 min. At 85° C., butylamine (1 ml, 10 mmol) dissolved in 7 ml of EtOAc was added dropwise during 15 min. The stirring continued for 1 hour at 100° C. The mixture was then hydrolyzed by adding 20 ml of 1N HCl at 50° C. and stirring for 0.5 hour at 50° C. The organic layer was separated. The aqueous layer was extracted with ethyl acetate. The combined organic layers were washed until neutral, dried with anhydrous sodium sulphate. The solven was removed in vacu. The crude products were purified by flash column chromatography eluting with hexane-EtOAc. Yellow powder was obtained in 49% yield. $^1$H NMR (300 MHz, CDCl$_3$): δ 2.16 (3H, s), 3.94 (3H, s), 5.63 (H, s), 6.33 (H, d, J=15.9 Hz), 6.92 (H, d, J=8.1 Hz), 7.01 (H, d, J=1.8 Hz), 7.10 (H, dd, J=8.1 Hz, J=1.8 Hz), 7.53 (H, d, J=15.9 Hz).

LL-17: At 80° C., LL-1 (468, 2 mmol) and boric anhydride (100 mg, 1.4 mmol) were dissolved in 10 ml of EtOAc. The solution was stirring for 1 hour. To the mixture, 10 ml of EtOAc solution containing 3,4-dimethoxybenzaldehyde (365 mg, 2.2 mmol) and tributyl borate (0.54 ml, 2 mmol) was added. After stirring for 0.5 hour, piperidine (0.08 ml) was added to the mixture. After stirring for 2 hours, 4 ml of 0.4 N HCl was added at 50° C. The mixture was vigorously stirred at 50° C. for 0.5 hour. The combined organic layers were washed until neutral, dried with anhydrous sodium sulphate. The solven was removed in vacu. The crude products were purified to offer 67.2 mg LL-17 in 8.8% yield. ESI-MS m/z 381.1 (M−1)$^+$ $^1$H NMR (300 MHz, CDCl$_3$): δ 3.94 (9H, s), 5.81 (H, s), 6.48 (2H, d, J=12.6 Hz), 6.87-7.14 (6H, m), 7.60 (2H, d, J=12.6 Hz).

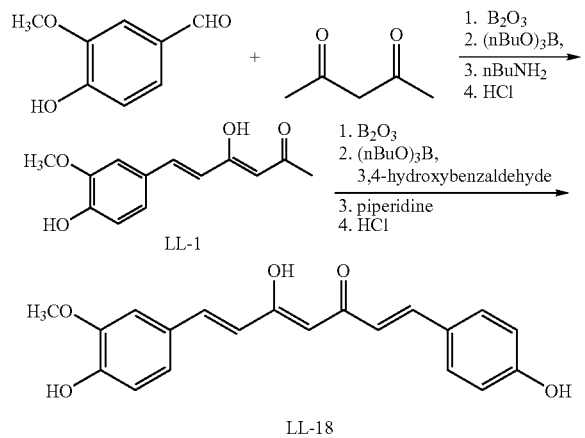

LL-18

LL-18: the same procedure as the preparation of LL-17.50% yield (started with LL-1 and 4-hydroxybenzaldehyde). Orange powder. ESI-MS m/z 337.1 (M−1)$^+$; $^1$H NMR (300 MHz, CD$_3$COCD$_3$): δ 3.93 (3H, s), 5.98 (H, s), 6.70 (2H, d, J=15.9 Hz), 6.87-6.92 (3H, m), 7.19 (H, dd, J=8.4 Hz, J=1.8 Hz), 7.35 (H, d, J=1.8 Hz), 7.56-7.64 (4H, m).

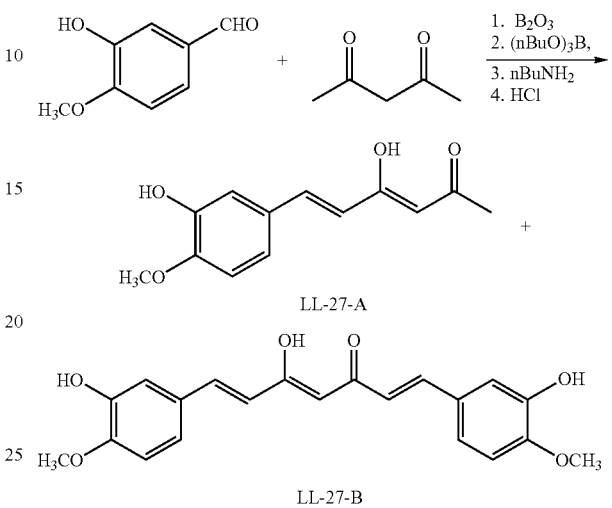

LL-27-B: Acetylacetone (3.1 ml, 30 mmol) and boric anhydride (1.5 g, 21 mmol) were dissolved in 20 ml of ethyl acetate. The solution was stirred at 70° C. for 0.5 hour. 3-hydroxy-4-methoxybenzaldehyde (1.52 g, 10 mmol) and tributyl borate (2.7 ml, 10 mmol) were added. The mixture was stirred for 30 min at 70° C. Then butylamine (1 ml, 10 mmol) dissolved in 7 ml of EtOAc was added dropwise during 15 min at 85° C. The stirring continued for 1 hour at 100° C. The mixture was then hydrolyzed by adding 20 ml of 1N HCl and stirring for 0.5 hour at 50° C. The organic layer was separated. The aqueous layer was extracted with ethyl acetate. The combined organic layers were washed until neutral, dried with anhydrous sodium sulphate. The solvent was removed in vacu. The crude products were purified. 1.04 g LL-27-A and 248 mg LL-27-B were obtained. ESI-MS m/z 367.1 (M−1)$^+$; $^1$H NMR (300 MHz, CD$_3$COCD$_3$): δ 4.01 (6H, s), 6.01 (H, s), 6.66 (2H, d, J=15.6 Hz), 7.03 (2H, d, J=8.1 Hz), 7.20 (2H, dd, J=2.1 Hz, J=8.1 Hz), 7.26 (2H,d, J=2.1 Hz), 7.65 (2H, d, J=15.3 Hz).

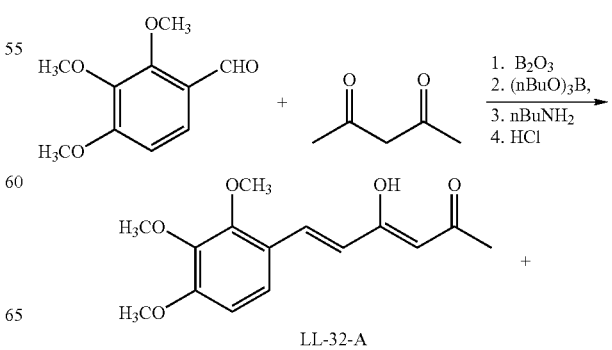

LL-32-A

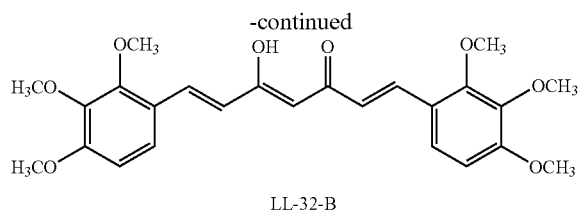

LL-32-B

LL-32-B: Acetylacetone (3.1 ml, 30 mmol) and boric anhydride (1.5 g, 21 mmol) were dissolved in 20 ml of ethyl acetate. The solution was stirred at 70° C. for 0.5 hour. 2,3,4-trimethoxybenzaldehyde (1.96 g, 10 mmol) and tributyl borate (2.7 ml, 10 mmol) were added. The mixture was stirred for 30 min at 70° C. Then butylamine (1 ml, 10 mmol) dissolved in 7 ml of EtOAc was added dropwise during 15 min at 85° C. The stirring continued for 1 hour at 100° C. The mixture was then hydrolyzed by adding 20 ml of 1N HCl and stirring for 0.5 hour at 50° C. The organic layer was separated. The aqueous layer was extracted with ethyl acetate. The combined organic layers were washed until neutral, dried with anhydrous sodium sulphate. The solvent was removed in vacu. The crude products were purified. 1.25 g LL-32-A and 150 mg LL-32-B were obtained. $^1$H NMR (300 MHz, CDCl$_3$): δ 3.89 (6H, s), 3.90 (6H, s), 3.94 (6H, s), 5.83 (H, s), 6.64 (2H, d, J=15.9 Hz), 6.71 (2H, d, J=9 Hz), 7.31 (2H, d, J=8.7 Hz), 7.85 (2H, d, J=16.2 Hz).

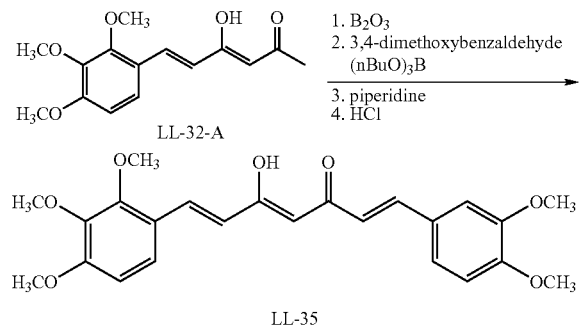

LL-35

LL-35: The same procedure as the preparation of LL-17. 55% yield (started with LL-32-A and 3,4-dimethoxybenzaldehyde). ESI-MS m/z 427.2 (M+H)$^+$, 449.3 (M+Na)$^+$; $^1$H NMR (300 MHz, CDCl$_3$): δ 3.89 (3H, s), 3.91 (3H, s), 3.93 (3H, s), 3.94 (6H, s), 5.83 (H, s), 6.51 (H, d, J=15.9 Hz), 6.63 (H, d, J=15.9 Hz), 6.71 (H, d, J=8.7 Hz), 6.89 (H, d, J=8.4 Hz), 7.09 (H, d, J=2.1 Hz), 7.15 (H, dd, J=1.8 Hz, J=8.7 Hz), 7.31 (H, d, J=8.7 Hz), 7.61 (H, d, J=15.9 Hz), 7.85 (H, d, J=16.2 Hz).

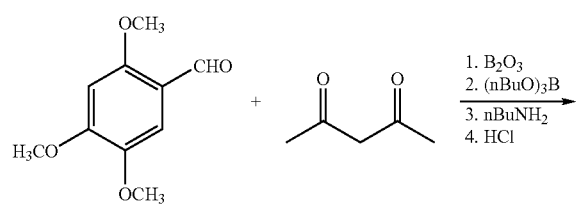

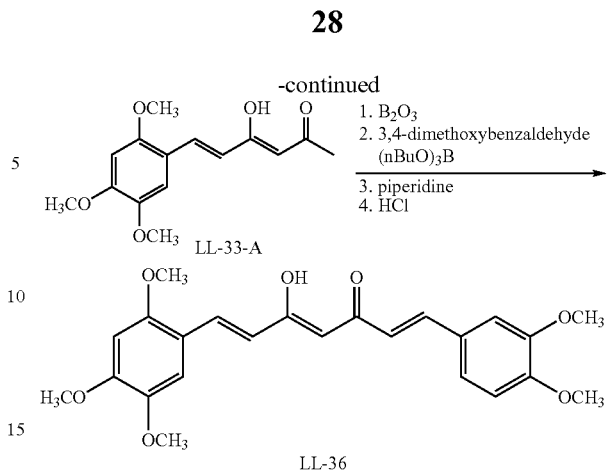

LL-36

LL-36: The same procedure as the preparation of LL-17. 48% yield (started with LL-33-A and 3,4-dimethoxybenzaldehyde). ESI-MS m/z 427.2 (M+H)$^+$, 449.3 (M+Na)$^+$; $^1$H NMR (300 MHz, CDCl$_3$): δ 3.89 (3H, s), 3.90 (3H, s), 3.93 (3H, s), 3.94 (3H, s), 3.95 (3H, s), 5.84 (H, s), 6.50 (H, d, J=15.6 Hz), 6.51 (H, s), 6.57 (H, d, J=16.2 Hz), 6.88 (H, d, J=8.1 Hz), 7.06 (H, s), 7.08 (H, d, J=2.1 Hz), 7.14 (H, dd, J=2.1 Hz, J=8.1 Hz), 7.60 (H, d, J=15.9 Hz), 7.96 (H, d, J=15.9 Hz).

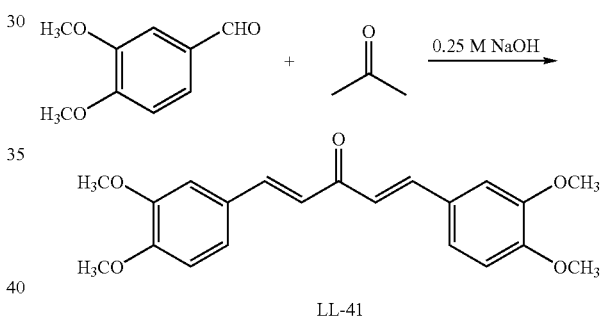

LL-41

LL-41: To a solution of acetone (0.36 ml, 5 mmol) and 3,4-dimethoxybenzaldehyde (1.66 g, 10 ml) in 50 ml of a 0.25 M solution of aqueous NaOH was added 1.5 ml of a 25% w/w aqueous solution of cetyltrimethylammonium bromide. The mixture was allowed to stir vigorously at room temperature for 20 hours, diluted with brine and extracted with ethyl acetate. The ethyl acetate solution was concentrated and then underwent column chromatography. 1.34 g bright yellow powder was obtained. 75% yield. ESI-MS m/z 355.2 (M+H)$^+$; $^1$H NMR (300 MHz, CD$_3$COCD$_3$): δ 3.94 (6H, s), 3.96 (6H, s), 6.90 (2H, d, J=8.4 Hz), 6.95 (2H, d, J=15.9 Hz), 7.15 (2H, d, J=1.8 Hz), 7.20 (2H, dd, J=1.8 Hz, J=8.4 Hz), 7.69 (2H, d, J=15.9 Hz).

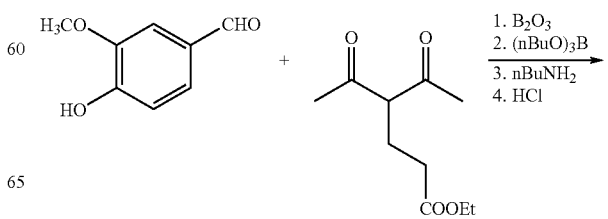

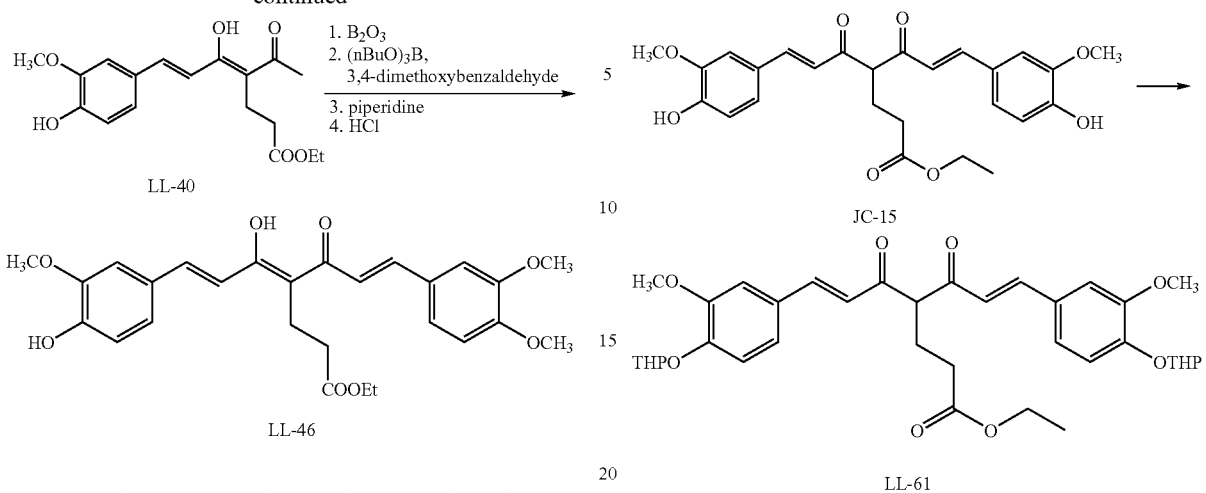

LL-46: The same procedure as the preparation of LL-17. 38% yield (started with LL-40 and 3,4-dimethoxybenzaldehyde). ESI-MS m/z 483.4 (M+H)$^+$; $^1$H NMR (300 MHz, CDCl$_3$): δ 1.25 (3H, t, J=7.2 Hz), 2.32-2.37 (2H, m), 2.55 (2H, t, J=7.8 Hz), 2.95 (0.5H, t, J=7.8 Hz), 3.91-3.97 (9H, m), 4.14 (2H, q, J=7.2 Hz), 6.70 (H, dd, J=4.2 Hz, J=15.6 Hz), 6.84-7.19 (7H, m), 7.62-7.76 (2H, m);

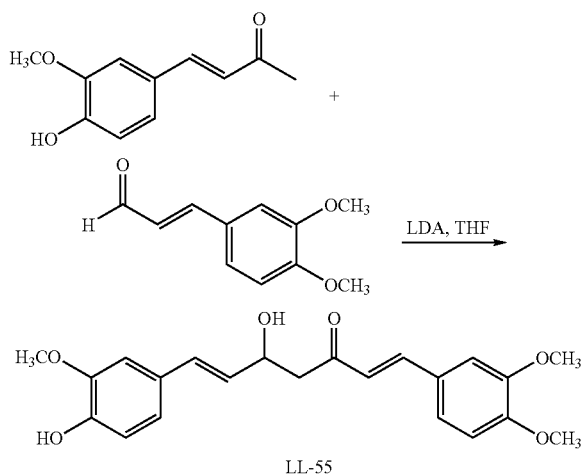

LL-55: To a stirred solution of LDA (0.29 ml, 2M hex/THF, 0.58 mmol) in 3 ml of THF at −78° C. was added a solution of 3,4-dimethoxycinnamone (100 mg, 0.48 mmol) in THF (3 ml). After 15 min, 3,4-dimethoxycinnamaldehyde (85 mg, 0.44 mmol) in THF (3 ml) was added. The mixture was stirred for 20 min at −78° C. And then the mixture was quenched with saturated NH$_4$Cl. The solution was allowed to warm to ambient temperature and extracted with ethyl acetate. 22 mg LL-55 was obtained by column chromatography. 13% yield. $^1$H NMR (300 MHz, CD$_3$COCD$_3$): δ 2.93 (2H, d), 3.80 (6H, s), 3.85 (6H, s), 4.13 (H, d), 6.25 (H, dd, J=6 Hz, J=15.9 Hz), 6.58 (H, d, J=15.9 Hz), 6.80 (H, d, J=16.2 Hz), 6.88 (H, d, J=8.7 Hz), 6.90 (H, dd, J=0.9 Hz, J=8.7 Hz), 7.00 (H, d, J=8.4 Hz), 7.04 (H, d, J=0.9 Hz), 7.25 (H, dd, J=0.9 Hz, J=8.7 Hz), 7.34 (H, d, J=0.9 Hz), 7.61 (1H, d, J=16.2 Hz).

LL-61: 4-thoxycarbonylethyl curcumin (153.1 mg, 0.33 mmol) and dihydropyran (0.73 mL, 7.32 mmol) were dissolved in 3 mL of dry dichloromethane containing PPTS (8.3 mg, 0.033 mmol). The solution was stirred at room temperature for 48 hours. The solution was then washed by water. The solvent was removed in vacu. The crude products was purified by CombiFlash® chromatography eluting with hexane-EtOAc to give LL-61 (134 mg), 59% yield, yellow powder, mp 60-61° C.; ESI MS m/z 635.2 (M−1)$^+$; $^1$H NMR (300 MHz, CDCl$_3$): δ 1.25 (3H, t), 1.57-2.17 (12H, m), 2.96 (0.57H, t), 3.62 (4H, t), 3.91 (6H, s), 4.13 (2H, q), 5.47 (2H, t), 6.72 (2H, d, J=15.6 Hz), 6.90-7.18 (6H, m), 7.44 (2H, d, J=15.6 Hz);

LL-62: A DMF solution (2 mL) of 1,7-bis-(3,4-dimethoxyphenyl)-4-methyl-1,6-heptadiene-3,5-dione (50.3 mg, 0.12 mmol) was added to an oil-free suspension of NaH (10 mg of 60%, 6 mg, 0.4 mmol) in DMF (2 mL) under nitrogen at 0° C. The solution was stirred at 0° C. for 30 min and then at room temperature for 2 h. To the sodium salt solution Selectfluoro™ (86.7 mg, 0.25 mmol) in DMF (2 mL) was added. After stirring for 2 h, the solution was extracted with EtOAc and washed with 5% H$_2$SO$_4$ (10 mL) and subsequently saturated NaHCO$_3$ solution (10 mL). Then the solvent was evaporated in vacuo. The crude products were purified by flash column chromatography eluting with hexane-EtOAc to afford LL-62 (25 mg) in 49% yield. yellow powder. $^1$H NMR (300 MHz, CDCl$_3$): δ 1.97 (3H, s), 3.90 (6H, s), 3.95 (6H, s), 6.83 (2H, d, J=7.8 Hz), 6.87 (2H, dd, J=3 Hz, J=15.6 Hz), 6.90(2H, d, J=1.8 Hz), 6.95 (2H, dd, J=1.8 Hz, J=7.8 Hz), 7.75 (2H, d, J=15.6 Hz);

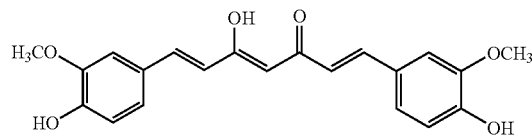

Curcumin

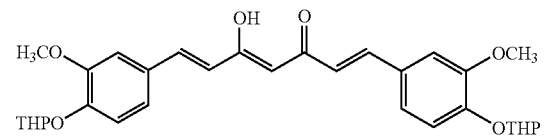

LL-64-B

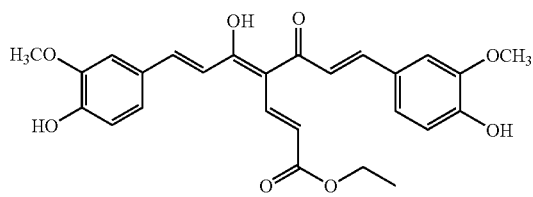

LL-66

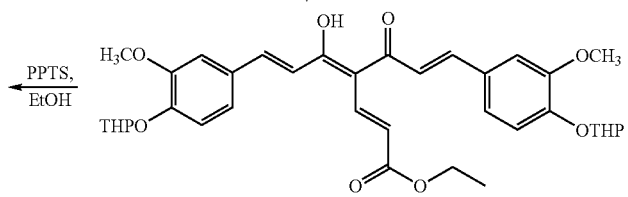

LL-65

LL-64B: Recrylstalized curcumin (1.08 g, 2.94 mmol) and dihydropyran (2 mL, 20 mmol) were dissolved in 30 mL of dry dichloromethane containing PPTS (74 mg, 0.29 mmol). The solution was stirred at room temperature for 24 hours. The solution was then washed by water. The solvent was removed in vacuo. The crude products was purified by CombiFlash® chromatography eluting with hexane-EtOAc to give LL-64B (1.12 g), 66.8% yield, yellow powder; ESI MS m/z 535.0 (M−1)$^+$; $^1$H NMR (300 MHz, CDCl$_3$): δ 1.57-2.17 (12H, m), 3.62 (4H, t), 3.91 (6H, s), 5.47 (2H, t), 5.83 (1H, s), 6.50 (2H, d, J=15.9 Hz), 7.09-7.16 (6H, m), 7.60 (2H, d, J=15.9 Hz); Anal. Calcd (theoretical) for C$_{31}$H$_{36}$O$_8$·¼H$_2$O: C, 68.81; H, 6.80. Found: C, 68.86; H, 6.83.

LL-65: A THF solution (3 mL) of LL-64B (55 mg, 0.10 mmol) was added to an oil-free suspension of NaH (7 mg of 60%, 4.2 mg, 0.17 mmol) in THF (2 mL) under nitrogen at 0° C. The solution was stirred at 0° C. for 30 min and then at room temperature for 2 h. To the sodium salt solution ethyl propiolate (0.02 mL, mmol) was added. After stirring for 2 h, the solution was extracted with EtOAc and washed with 5% H$_2$SO$_4$ (10 mL) and subsequently saturated NaHCO$_3$ solution (10 mL). Then the solvent was evaporated in vacuo. The crude products were purified by CombiFlash® chromatography eluting with hexane-EtOAc to afford LL-65 (39.4 mg) 62% yield, orange powder; mp 72-73° C.; ESI MS m/z 634.7 M$^+$; $^1$H NMR (300 MHz, CDCl$_3$): δ 1.34 (3H, t), 1.5-2.2 (12H, m), 3.62 (4H, t), 3.92 (6H, s), 4.28 (2H, q), 5.49 (2H, t) 5.96 (H, d, J=15.6 Hz), 7.00 (2H, d, J=15.6 Hz), 7.08-7.16 (6H, m), 7.76 (2H, d, J=15.3 Hz), 7.83 (H, d, J=15.9 Hz); Anal. Calcd (theoretical) for C$_{36}$H$_{42}$O$_{10}$l: C, 68.12; H, 6.67. Found: C, 67.82; H, 6.73.

LL-66: The EtOH (2.5 mL) solution of LL-65 (14.8 mg, 0.023 mmol) and PPTS (5 mg, 0.02 mmol) was stirred at room temperature for 3 h. The solution was evaporated in vacuo. LL-66 (10 mg) was obtained by CombiFlash® chromatography eluting with hexane-EtOAc. 93% yield, orange powder, mp 106-106.5° C.; ESI MS m/z 465.2 (M−1)$^+$; $^1$H NMR (300 MHz, CDCl$_3$): δ 1.34 (3H, t), 3.95 (6H, s), 4.29 (2H, quart), 5.96 (2H, d, J=15.6 Hz), 6.95 (2H, d, J=8.2 Hz), 6.96 (1H, d, J=15.6 Hz), 7.05 (2H, d, J=2.1 Hz), 7.17 (2H, dd, J=8.2 Hz, J=2.1 Hz), 7.75 (2H, d, J=15.3 Hz), 7.90 (1H, d, J=15.9 Hz).

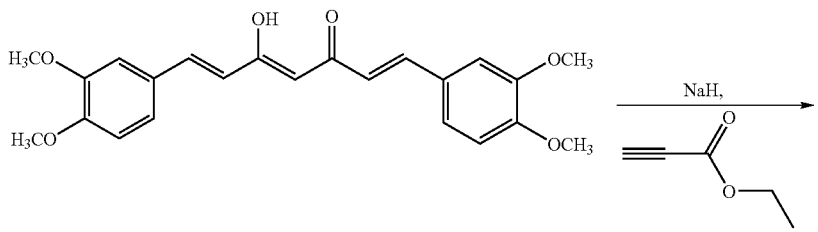

-continued

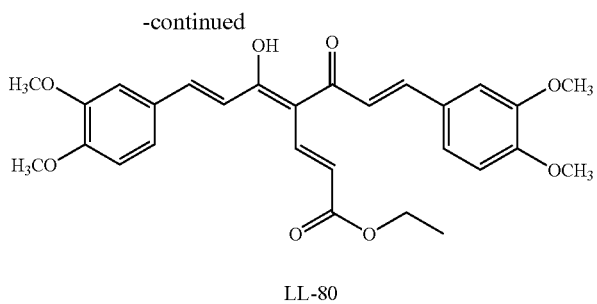

LL-80

LL-80: The same synthetic procedure as the preparation of LL-66. 62% yield (started with 1,7-bis(3,4-dimethoxyphenyl)-1,6-pentadiene-3,6-dione). Red powder. $^1$H NMR (300 MHz, CDCl$_3$): δ 1.34 (3H, t), 3.95 (12H, s), 4.29 (2H, quart), 5.98 (2H, d, J=15.6 Hz), 6.95 (2H, d, J=8.4 Hz), 7.00 (1H, d, J=15.6 Hz), 7.08 (2H, d, J=1.8 Hz), 7.22 (2H, dd, J=8.4 Hz, J=1.8 Hz), 7.77 (2H, d, J=15.3 Hz), 7.91 (1H, d, J=15.6 Hz).

HOJ-7: 3% yield (started with 5 mmol of 2,4-difluorobenzaldehyde), yellow powder, mp 155.5-156° C. (n-hexane-EtOAc). $^1$H NMR (CDCl$_3$) δ5.86 (1H, s), 6.68 (2H, d, J=16.0 Hz), 6.84-6.96 (4H, m), 7.56 (2H, m), 7.71 (2H, d, J=16.0 Hz). ESI-MS m/z 347 [M−1]$^+$. Anal. calcd for C$_{19}$H$_{12}$F$_4$O$_2$: C, 65.52; H, 3.47. Found: C, 65.66; H, 3.57.

HOJ-9: 10% yield (started with 5 mmol of 2-fluoro-4-methoxybenzaldehyde), yellow powder, mp 163-165° C. (n-hexane-EtOAc). $^1$H NMR (CDCl$_3$) δ3.84 (6H, s), 5.82 (1H, s), 6.62 (2H, d, J=16.0 Hz), 6.70 (4H, m), 7.48 (2H, t, J=8.7 Hz), 7.71 (2H, d, J=16.0 Hz). ESI-MS m/z 371 [M−1]$^+$. Anal. calcd for C$_{21}$H$_{18}$F$_2$O$_4$: C, 67.74; H, 4.87. Found: C, 67.58; H, 4.92.

HOJ-10: 9% yield (started with 5 mmol of 2-fluoro-6-methoxybenzaldehyde), yellow needles, mp 144-145° C. (n-hexane-EtOAc). $^1$H NMR (CDCl$_3$) δ3.82 (6H, s), 5.90 (1H, s), 6.72 (2H, d, J=16.0 Hz), 6.88 (2H, m), 7.56 (2H, m), 7.00-7.07 (4H, m), 7.74 (2H, d, J=16.0 Hz). ESI-MS m/z 371 [M−1]$^+$. Anal. calcd for C$_{21}$H$_{18}$F$_2$O$_4$: C, 67.74; H, 4.87. Found: C, 67.60; H, 4.95.

Biological activity. The compounds shown above are screened as follows and found to have anticancer and anti-androgen receptor activity as shown in Table 2 below.

Cell culture and transfection—Human prostate cancer LNCaP and PC-3 cells were maintained in RPMI medium and Dulbecco's minimum essential medium (DMEM), respectively. Both media were strengthened with penicillin (25 units/mL), streptomycin (25 μg/mL), and 10% fetal calf serum. Androgen receptor transactivation assay, an androgen-dependent reporter gene transcription test, was employed as the primary screening for potential antiandrogen identification. This assay was first performed in LNCaP cells, which express a clinically relevant mutant AR. Once potential compounds were indicated by LNCaP AR transactivation assay, they were re-examined for their potential activity against wild type AR. Wild type AR transactivation assay was performed in PC-3 host cells, which lack an endogenous, functional AR.

Our previously described conditions for cell transfection were followed (Ohtsu et al, J Medicinal Chem 45: 5037-5042 (2002); Ohtsu et al., Bioorganic & Medicinal Chemistry 11:5083-5090 (2003)). In brief, cells were plated in 24- or 48-well tissue culture dishes twenty-four (PC-3 cells) or forty-eight (LNCaP cells) hours prior to transfection. Subsequently, LNCaP cells were transfected with a reporter gene, MMTV-luciferase, which contains MMTV-LTR promoter and androgen receptor binding element, and PRL-SV40, which served as an internal control for transfection efficiency. PC-3 cells were transfected with a wild type AR expression plasmid, pSG5AR, in addition to the above-mentioned MMTV-luciferase reporter gene and PRL-SV40 internal control. SuperFect (Qiagen, Chatsworth, Calif.) was employed as the transfection reagent following manufacturer's recommendations. At the end of a five-hour transfection, the medium was changed to DMEM or RPMI supplemented with 10% charcoal dextran-stripped, androgen-depleted serum. Twenty-four hours later, the cells were treated with 1 nM of DHT and/or test compounds at the designated concentration for another twenty-four hours. The cells were harvested for luciferase activity assay using Dual Luciferase Assay System (Promega, Madison, Wis.). The derived data were expressed as relative luciferase activity normalized to the internal luciferase control. DHT incubation induced a marked expression of reporter gene. Test compounds capable of significantly suppressing this androgen-induced reporter gene expression were identified as potential anti-androgens.

LNCaP cell growth assay: As mentioned above, LNCaP cells contain a substantial amount of mutant AR, and thus these cells' growth can be significantly activated upon androgen incubation. LNCaP cell growth assay thus was used as an alternative to confirm potential antiandrogens identified by the above-mentioned AR transactivation assay. An MTT analysis, relying upon the conversion of a colorless substrate to reduced tetrazolium by the mitochondrial dehydrogenase, was used. The experimental conditions were detailed elsewhere (Ohtsu et al., Bioorganic & Medicinal Chemistry 11:5083-5090 (2003)). Briefly, cells were plated in 96-well tissue culture plates and then incubated for 5 consecutive days in the presence of 1 nM of DHT and/or test compounds in 10% charcoal dextran-stripped serum-containing RPMI. At the end of incubation, the cells were given MTT (5 mg/ml in PBS) for three hours at 37° C. The resultant precipitate was dissolved in a lysis buffer and then quantitated at a wavelength of 595 nm using a microplate reader. To ensure the accuracy of data derived from the MTT analysis, cell count was performed using duplicate samples. Test compounds that displayed an adverse effect on the androgen-induced prostate tumor cell growth were identified as potential antiandrogens.

TABLE 2

The anti-AR activity of curcumin analogues.

| Compound | wrAR/PC3 | LNCaP |
|---|---|---|
| LL-7 | 0 | + |
| LL-10 | 0 | + |
| LL-17 | + | 0 |
| LL-18 | + | 0 |
| LL-27B | + | 0 |
| LL-32B | + | 0 |
| LL-35 | + | 0 |
| LL-36 | + | 0 |
| HOJ-7 | + | + |
| HOJ-9 | + | 0 |
| HOJ-10 | + | + |
| LL-41 | + | + |
| LL-46 | + | + |
| LL-55 | 0 | + |
| LL-61A | + | + |
| LL-62 | 0 | + |
| LL-65/LL-80 | ++ | ++ |
| LL-66 | 0 | + |

The foregoing is illustrative of the present invention, and is not to be construed as limiting thereof. The invention is defined by the following claims, with equivalents of the claims to be included therein.

What is claimed is:

1. A compound according to formula II:

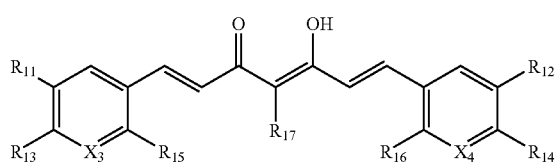

(II)

wherein:
$R_{11}$ and $R_{12}$ are each independently selected from the group consisting of alkoxy, nitro, amino, and dialkylamino;
$R_{13}$ and $R_{14}$ are each independently selected from the group consisting of hydroxy, alkoxy, —$OR_{18}C(O)R_{19}$ wherein $R_{18}$ is lower alkylene or alkenylene and $R_{19}$ is alkoxy, and tetrahydropyranyl[THP];
or $R_{11}$ and $R_{13}$ together are alkylenedioxy;
or $R_{12}$ and $R_{14}$ together are alkylenedioxy;
$R_{15}$ and $R_{16}$ are each independently selected from the group consisting of H, halogen, and nitro;

$R_{17}$ is —$R_{20}C(O)OR_{21}$, wherein $R_{20}$ is alkylene or alkenylene and $R_{21}$ is H or alkyl;
$X_3$ is N, or $X_3$ is C bonded to a H, alkoxy or nitro; and
$X_4$ is N, or $X_4$ is C bonded to a H, alkoxy or nitro;
or a pharmaceutically acceptable salt thereof, subject to the proviso that
$R_{20}$ is not alkylene when $R_{11}$, $R_{12}$, $R_{13}$ and $R_{14}$ are methoxy, and $X_3$ and $X_4$ are C bonded to a methoxy.

2. The compound according to claim 1, wherein $R_{11}$ and $R_{12}$ are each independently selected from the group consisting of alkoxy, nitro, amino, and dimethylamino.

3. The compound according to claim 1, wherein $R_{11}$ and $R_{13}$ together are methylenedioxy or ethylenedioxy.

4. The compound according to claim 1, wherein $R_{12}$ and $R_{14}$ together are methylenedioxy or ethylenedioxy.

5. The compound according to claim 1, wherein $R_{15}$ and $R_{16}$ are each independently selected from the group consisting of H, F, and nitro.

6. A pharmaceutical formulation comprising a compound according to claim 1 in a pharmaceutically acceptable carrier.

7. The pharmaceutical formulation according to claim 6, wherein said carrier is an aqueous carrier.

8. The compound according to claim 1 having the structure:

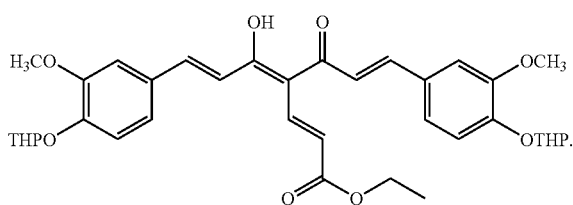

9. The compound according to claim 1 having the structure:

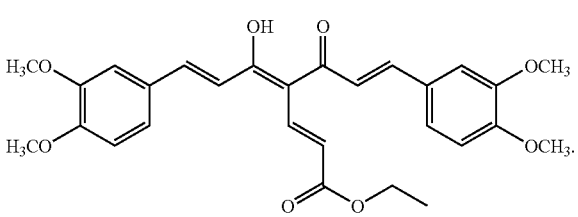

* * * * *

UNITED STATES PATENT AND TRADEMARK OFFICE
CERTIFICATE OF CORRECTION

PATENT NO.         : 7,355,081 B2
APPLICATION NO.    : 10/966723
DATED              : April 8, 2008
INVENTOR(S)        : Lee et al.

Page 1 of 1

It is certified that error appears in the above-identified patent and that said Letters Patent is hereby corrected as shown below:

<u>Item 54 on Title Page, and Column 1, line 1:</u>

Please correct Title to read -- NOVEL CURCUMIN ANALOGUES AND USES THEREOF --

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,355,081 B2
APPLICATION NO. : 10/966723
DATED : April 8, 2008
INVENTOR(S) : Kuo-Hsiung Lee et al.

Page 1 of 1

It is certified that error appears in the above-identified patent and that said Letters Patent is hereby corrected as shown below:

Title Page,
Item [54], Title, the word "NOVEL" (as inserted by Certificate of Correction issued August 5, 2008) should be deleted and title is to be reinstated to read -- CURCUMIN ANALOGUES AND USES THEREOF --.

Signed and Sealed this

Twenty-sixth Day of August, 2008

JON W. DUDAS
*Director of the United States Patent and Trademark Office*